United States Patent
Wong et al.

(10) Patent No.: US 11,033,608 B2
(45) Date of Patent: *Jun. 15, 2021

(54) INSULIN PREMIX FORMULATION AND PRODUCT, METHODS OF PREPARING SAME, AND METHODS OF USING SAME

(71) Applicants: Baxter International, Inc., Deerfield, IL (US); Baxter Healthcare SA, Glattpark (Opfikon) (CH)

(72) Inventors: Joseph Chung Tak Wong, Williamsville, NY (US); Sarah Elizabeth Lee, Buffalo Grove, IL (US)

(73) Assignees: Baxter International, Inc., Deerfield, IL (US); Baxter Healthcare SA, Glattpark (Opfikon) (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/066,067

(22) Filed: Oct. 8, 2020

(65) Prior Publication Data

US 2021/0052704 A1    Feb. 25, 2021

Related U.S. Application Data

(63) Continuation of application No. 16/681,392, filed on Nov. 12, 2019, now Pat. No. 10,799,564.

(60) Provisional application No. 62/843,881, filed on May 6, 2019, provisional application No. 62/862,573, filed on Jun. 17, 2019.

(51) Int. Cl.
| | |
|---|---|
| *A61K 38/28* | (2006.01) |
| *A61J 1/10* | (2006.01) |
| *A61J 1/14* | (2006.01) |
| *A61K 47/02* | (2006.01) |
| *A61L 31/06* | (2006.01) |
| *A61L 31/14* | (2006.01) |

(52) U.S. Cl.
CPC .............. *A61K 38/28* (2013.01); *A61J 1/10* (2013.01); *A61J 1/1468* (2015.05); *A61K 47/02* (2013.01); *A61L 31/06* (2013.01); *A61L 31/14* (2013.01)

(58) Field of Classification Search
CPC ...... A61K 38/28; C07K 14/62; C07K 14/622; A61J 1/10; A61J 1/14; A61J 1/1406; A61J 1/1468
See application file for complete search history.

(56) References Cited

U.S. PATENT DOCUMENTS

| | | | |
|---|---|---|---|
| 1,469,994 A | 10/1923 | Banting et al. | |
| 2,143,590 A | 1/1939 | Scott | |
| 2,143,591 A | 1/1939 | Scott et al. | |
| 2,882,203 A | 4/1959 | Petersen et al. | |
| 3,929,995 A | 12/1975 | Kawashima | |
| 4,423,039 A | 12/1983 | Albisser | |
| 5,747,445 A | 5/1998 | Backstrom | |
| 6,342,227 B1 | 1/2002 | Thivolet | |
| 6,489,292 B1 | 12/2002 | Havelund | |
| 7,608,583 B2 | 10/2009 | Sahib et al. | |
| 7,998,927 B2 | 8/2011 | Maggio | |
| 8,394,766 B2 | 3/2013 | McCarthy et al. | |
| 8,426,362 B2 | 4/2013 | Surolia et al. | |
| 8,575,322 B2 | 11/2013 | Manoj et al. | |
| 8,889,103 B2 | 11/2014 | Hay | |
| 9,309,281 B2 | 4/2016 | Manoj et al. | |
| 9,839,692 B2 | 12/2017 | Bley | |
| 9,993,555 B2 | 6/2018 | Akers et al. | |
| 10,000,544 B2 | 6/2018 | Krishnan et al. | |
| 10,799,564 B1 * | 10/2020 | Wong ................... | A61K 9/0019 |
| 2007/0207983 A1 | 9/2007 | Nieuwenhuizen | |
| 2008/0311321 A1 | 12/2008 | Sparholt | |
| 2009/0060861 A1 | 3/2009 | Poulsen | |
| 2011/0318779 A1 | 12/2011 | Shin | |
| 2013/0274342 A1 | 10/2013 | Ginski | |
| 2015/0273022 A1 | 10/2015 | Wilson et al. | |
| 2016/0129087 A1 | 5/2016 | Christe et al. | |
| 2018/0044395 A1 | 2/2018 | Gant et al. | |

(Continued)

FOREIGN PATENT DOCUMENTS

| | | |
|---|---|---|
| WO | 2017052305 | 3/2017 |
| WO | 2017126984 | 7/2017 |
| WO | 2018171535 | 9/2018 |

OTHER PUBLICATIONS

Search Report for PCT/US2020/031322 dated Jul. 30, 2020—6 pages.
Written Opinion of the International Search Authority for PCT/US2020/031322 dated Jul. 30, 2020—9 pages.

*Primary Examiner* — Jeffrey E. Russel
(74) *Attorney, Agent, or Firm* — K&L Gates LLP

(57) ABSTRACT

A pharmaceutically acceptable insulin premix formulation contains about 0.1-10.0 Unit/mL of insulin for intravenous administration and preferably further contains a tonicity adjuster. The methods for making and using such formulation are also provided. The pharmaceutically acceptable insulin premix formulation may be aseptically filled into a flexible container assembly to form a pharmaceutical insulin premix product. The insulin premix product can be a sterile and ready-to-use aqueous solution for glycemic control in an individual with metabolic disorders through intravenous infusion. The insulin premix product is unexpectedly stable when freshly prepared and also during its shelf-life of storage at refrigeration temperatures of 2° C. to 5° C. for 24 months followed by additional 30 days at room temperatures of 23° C. to 27° C., even without any added preservative, any added zinc, any added surfactant or any other added stabilizing excipient.

23 Claims, 37 Drawing Sheets

Specification includes a Sequence Listing.

(56) References Cited

U.S. PATENT DOCUMENTS

2018/0078645 A1 3/2018 Gerring et al.
2018/0105570 A1 4/2018 Balcerek et al.
2018/0291077 A1 10/2018 Choi et al.
2019/0322719 A1 10/2019 Weiss

* cited by examiner

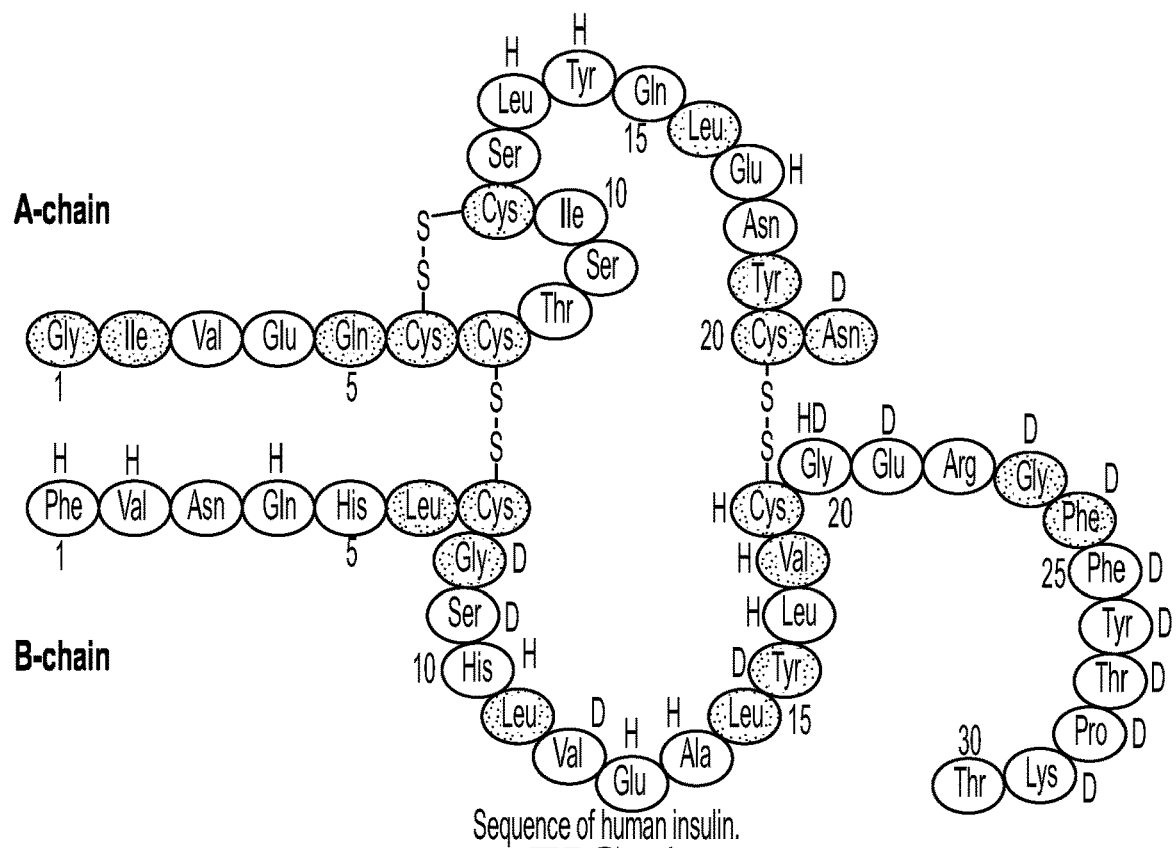

Sequence of human insulin.

FIG. 1

| Description | Inner Surface Contacting Insulin Premix |
|---|---|
| Container 1 | PP Copolymer, Ultra Low Density Polyethylene and (Styrene-Ethylene/Butadiene-Styrene) Block Copolymer |
| Container 2 | Polyvinyl Chloride (PVC) |
| Container 3 | Linear Low Density Polyethylene (LLDPE) |
| Container 4 | GALAXY® PL2501: Polyethylene (PE) |
| Container 5 | PVC & DEHP free, no latex |
| Container 6 | PVC, no latex, contains DEHP |
| Container 7 | PVC & DEHP free, no latex |

Characteristics of the flexible plastic containers for insulin premix products.

FIG. 2

Method for preparing a pharmaceutically acceptable insulin premix formulation.

| Interval | | Time 0 | Time 0 | 4 Weeks | 4 Weeks | 8 Weeks | 8 Weeks | 12 Weeks | 12 Weeks |
|---|---|---|---|---|---|---|---|---|---|
| Sample ID | | Glass-PBS-2mM | PL2501-PBS-2mM | Glass-PBS-2mM | PL2501-PBS-2mM | Glass-PBS-2mM | PL2501-PBS-2mM | Glass-PBS-2mM | PL2501-PBS-2mM |
| Container | | Glass | PL2501 | Glass | PL2501 | Glass | PL2501 | Glass | PL2501 |
| Insulin Conc. (Unit/mL) | | 0.992 | 0.966 | 1.003 | 0.989 | 1.000 | 0.977 | 1.006 | 0.979 |
| Related Sub. (%) | A21 | 0.74 | 0.56 | NA | NA | NA | NA | NA | NA |
| | Insulin | 98.70 | 99.04 | 97.95 | 97.69 | 98.38 | 98.30 | 97.21 | 98.25 |
| | Other | 0.56 | 0.40 | NA | NA | NA | NA | NA | NA |
| HMWP (%) | Covalent | NA | NA | NA | NA | NA | NA | NA | NA |
| | Monomer | 99.7 | 99.7 | 99.8 | 99.8 | 99.8 | 99.81 | 99.56 | 99.6 |
| | Aggregate | 0.3 | 0.3 | 0.2 | 0.2 | 0.3 | 0.19 | 0.42 | 0.4 |
| | Fragment | NA | NA | NA | NA | 0.0 | 0 | 0.0 | 0.0 |
| pH | | 7.40 | 7.40 | 7.42 | 7.44 | 7.44 | 7.47 | 7.35 | 7.32 |
| Osmolality (mOsmo/kg) | | 293 | 294 | 293 | 294 | 294 | 294 | 292 | 292 |
| Instrumental PM ≥2 μm | | NA | 50 | NA | NA | NA | NA | NA | 12 |
| Instrumental PM NMT 25/mL ≥ 10 μm | | NA | 2 | NA | NA | NA | NA | NA | 0 |
| Instrumental PM NMT 3/mL ≥ 25 μm | | NA | 0 | NA | NA | NA | NA | NA | 0 |
| Visual Inspection | | Pass | Pass | Pass | Pass | Pass | Pass | Pass | Pass |

FIG. 7A

| Interval | | 24 Weeks | 24 Weeks | 62 Weeks | 62 Weeks | 110 Weeks | 110 Weeks |
|---|---|---|---|---|---|---|---|
| Sample ID | | Glass-PBS-2mM | PL2501-PBS-2mM | Glass-PBS-2mM | PL2501-PBS-2mM | Glass-PBS-2mM | PL2501-PBS-2mM |
| Container | | Glass | PL2501 | Glass | PL2501 | Glass | PL2501 |
| Insulin Conc. (Unit/mL) | | 0.996 | 0.975 | 0.980 | 0.952 | 0.938 | 0.896 |
| Related Sub. (%) | A21 | 0.50 | 0.48 | 0.52 | 0.49 | 3.058 | 3.238 |
| | Insulin | 96.80 | 96.12 | 97.58 | 97.58 | 94.10 | 93.13 |
| | Other | 2.70 | 3.40 | 1.90 | 1.93 | 2.844 | 3.628 |
| HMWP (%) | Covalent | 0.32 | 0.42 | 0.44 | 0.42 | 0.53 | 0.74 |
| | Monomer | 99.68 | 9a58 | 99.56 | 99.58 | 99.47 | 99.26 |
| | Aggregate | NA | NA | NA | NA | NA | NA |
| | Fragment | NA | NA | NA | NA | NA | NA |
| pH | | 7.37 | 7.28 | 7.22 | 7.21 | 7.23 | 7.27 |
| Osmolality (mOsmo/kg) | | 294 | 293 | 293 | 293 | 294 | 294 |
| Instrumental PM ≥2μm | | NA | 16 | NA | 88 | NA | 83 |
| Instrumental PM NMT 25/mL ≥ 10 μm | | NA | 0 | NA | 1 | NA | 1 |
| Instrumental PM NMT 3/mL ≥ 25 μm | | NA | 0 | NA | 0 | NA | 0 |
| Visual Inspection | | Pass | Pass | Pass | Pass | Pass | Pass |

Recombinant Human Insulin (1.0 U/mL) with PBS (Phosphate Buffer) Formulation in Glass Ampoules (Sample ID: Glass-PBS-2mM) and in PL2501 Galaxy Containers (PL2501-PBS-2mM) at 5±3°C Storage.

FIG. 7B

| Interval | | Time 0 | Time 0 | 4 Weeks | 4 Weeks | 8 Weeks | 8 Weeks | 12 Weeks | 12 Weeks |
|---|---|---|---|---|---|---|---|---|---|
| Sample ID | | Glass-Arginine-2mM | P12501-Arginine-2mM | Glass-Arginine-2mM | PL2501-Arginine-2mM | Glass-Arginine-2mM | PL2501-Arginine-2mM | Glass-Arginine-2mM | PL2501-Arginine-2mM |
| Container | | Glass | P12501 | Glass | P12501 | Glass | P12501 | Glass | PL2501 |
| Insulin Conc. (Unit/mL) | | 0.987 | 0.971 | 0.995 | 0.964 | 0.999 | 0.975 | 1.005 | 0.983 |
| Related Sub. (%) | A21 | 0.76 | 0.58 | NA | NA | NA | NA | NA | NA |
| | Insulin | 94.74 | 98.98 | 97.08 | 97.46 | 98.19 | 98.24 | 95.16 | 98.35 |
| | Other | 0.50 | 0.44 | NA | NA | NA | NA | NA | NA |
| HMWP (%) | Covalent | NA | NA | NA | NA | NA | NA | NA | NA |
| | Monomer | 99.7 | 99.7 | 99.8 | 99.8 | 99.6 | 99.6 | 99.81 | 99.62 |
| | Aggregate | 0.3 | 0.3 | 0.2 | 0.2 | 0.4 | 0.4 | 0.19 | 0.38 |
| | Fragment | NA | NA | NA | NA | 0.0 | 0.0 | 0.0 | 0.0 |
| pH | | 7.15 | 7.11 | 7.65 | 7.57 | 7.53 | 7.57 | 7.00 | 6.98 |
| Osmolality (mOsmo/kg) | | 293 | 293 | 293 | 294 | 294 | 293 | 291 | 291 |
| Instrumental PM ≥2 μm | | NA | NA | NA | NA | NA | NA | NA | 15 |
| Instrumental PM NMT 25/mL ≥ 10 μm | | NA | 1 | NA | NA | NA | NA | NA | 0 |
| Instrumental PM NMT 3/mL ≥ 25 μm | | NA | 0 | NA | NA | NA | NA | NA | 0 |
| Visual Inspection | | Pass | Pass | Pass | Pass | Pass | Pass | Pass | Pass |

FIG. 8A

| Interval | | 24 Weeks | 24 Weeks | 62 Weeks | 62 Weeks | 110 Weeks | 110 Weeks |
|---|---|---|---|---|---|---|---|
| Sample ID | | Glass-Arginine-2mM | PL2501-Arginine-2mM | Glass-Arginine-2mM | PL2501-Arginine-2mM | Glass-Arginine-2mM | PL2501-Arginine-2mM |
| Container | | Glass | PL2501 | Glass | PL2501 | Glass | PL2501 |
| Insulin Conc. (Unit/mL) | | 1.007 | 0.976 | 0.990 | 0.965 | 0.959 | 0.931 |
| Related Sub. (%) | A21 | 0.48 | 0.49 | 0.52 | 0.49 | 2.633 | 3.483 |
| | Insulin | 97.03 | 96.75 | 97.76 | 97.58 | 94.95 | 95.01 |
| | Other | 2.49 | 2.76 | 1.72 | 1.93 | 2.419 | 2.505 |
| HMW Protein (%) | Covalent | 0.39 | 0.39 | 0.38 | 0.34 | 0.47 | 0.50 |
| | Monomer | 99.61 | 99.61 | 99.62 | 99.66 | 99.53 | 99.50 |
| | Aggregate | NA | NA | NA | NA | NA | NA |
| | Fragment | NA | NA | NA | NA | NA | NA |
| pH | | 7.36 | 7.04 | 6.88 | 6.68 | 6.69 | 6.69 |
| Osmolality (mOsmo/kg) | | 291 | 292 | 293 | 291 | 292 | 293 |
| Instrumental PM ≥2μm | | NA | 8 | NA | 57 | NA | 50 |
| Instrumental PM NMT 25/mL ≥ 10 μm | | NA | 1 | NA | 2 | NA | 0 |
| Instrumental PM NMT 3/mL ≥ 25 μm | | NA | 0 | NA | 0 | NA | 0 |
| Visual Inspection | | Pass | Pass | Pass | Pass | Pass | Pass |

Recombinant Human Insulin (1.0 U/mL) with Arginine Formulation in Glass Ampoules (Sample ID: Glass-Arginine-2mM) and in PL2501 Galaxy Containers (PL2501-Arginine-2mM) at 5±3°C Storage.

FIG. 8B

| Interval | | Time 0 | Time 0 | 4 Weeks | 4 Weeks | 8 Weeks | 8 Weeks | 12 Weeks | 12 Weeks |
|---|---|---|---|---|---|---|---|---|---|
| Sample ID | | Glass-PBS-2mM-(KCl-4mM) | PL2501-PBS-2mM-(KCl-4mM) | Glass-PBS-2mM-(KCl-4mM) | PL2501-PBS-2mM-(KCl-4mM) | Glass-PBS-2mM-(KCl-4mM) | PL2501-PBS-2mM-(KCl-4mM) | Glass-PBS-2mM-(KCl-4mM) | PL2501-PBS-2mM-(KCl-4mM) |
| Container | | Glass | PL2501 | Glass | PL2501 | Glass | PL2501 | Glass | PL2501 |
| Insulin Con(Unit/mL) | | 0.987 | 0.987 | 1.015 | 0.988 | 1.017 | 0.952 | 0.993 | 0.957 |
| Related Sub. (%) | A21 | 0.65 | 0.59 | NA | NA | NA | NA | NA | NA |
| | Insulin | 98.89 | 99.00 | 97.71 | 97.52 | 96.23 | 98.24 | 98.28 | 97.39 |
| | Other | 0.46 | 0.41 | NA | NA | NA | NA | NA | NA |
| HMW Protein (%) | Covalent | NA | NA | NA | NA | NA | NA | NA | NA |
| | Monomer | 99.7 | 99.7 | 99.7 | 99.8 | 99.8 | 99.7 | 99.63 | 99.61 |
| | Aggregate | 0.3 | 0.3 | 0.3 | 0.2 | 0.4 | 0.3 | 0.37 | 0.39 |
| | Fragment | NA | NA | NA | NA | 0.0 | 0.0 | 0.0 | 0.0 |
| pH | | 7.38 | 7.40 | 7.39 | 7.43 | 7.44 | 7.49 | 7.35 | 7.27 |
| Osmolality (mOsmo/kg) | | 299 | 300 | 299 | 302 | 299 | 301 | 298 | 298 |
| Instrumental PM ≥2μm | | NA | NA | NA | NA | NA | NA | NA | 11 |
| Instrumental PM NMT 25/mL ≥ 10 μm | | NA | 1 | NA | NA | NA | NA | NA | 0 |
| Instrumental PM NMT 3/mL ≥ 25 μm | | NA | 0 | NA | NA | NA | NA | NA | 0 |
| Visual Inspection | | Pass | Pass | Pass | Pass | Pass | Pass | Pass | Pass |

FIG. 9A

| Interval | 24 Weeks | 24 Weeks | 62 Weeks | 62 Weeks | 110 Weeks | 110 Weeks |
|---|---|---|---|---|---|---|
| Sample ID | Glass-PBS-2mM-(KCl-4mM) | PL2501-PBS-2mM-(KCl-4mM) | Glass-PBS-2mM-(KCl-4mM) | PL2501-PBS-2mM-(KCl-4mM) | Glass-PBS-2mM-(KCl-4mM) | PL2501-PBS-2mM-(KCl-4mM) |
| Container | Glass | PL2501 | Glass | PL2501 | Glass | PL2501 |
| Insulin Conc. (Unit/mL) | 1.018 | 0.961 | 0.994 | 0.934 | 0.953 | 0.874 |
| Related Sub. (%) A21 | 0.51 | 0.49 | 0.50 | 0.57 | 3.087 | 3.114 |
| Related Sub. (%) Insulin | 96.61 | 96.30 | 97.67 | 97.27 | 94.233 | 93.05 |
| Related Sub. (%) Other | 2.88 | 3.20 | 1.83 | 2.16 | 2.68 | 3.83 |
| HMW Protein (%) Covalent | 0.36 | 0.31 | 0.44 | 0.54 | 0.52 | 0.67 |
| HMW Protein (%) Monomer | 99.64 | 99.69 | 99.56 | 99.46 | 99.48 | 99.33 |
| HMW Protein (%) Aggregate | NA | NA | NA | NA | NA | NA |
| HMW Protein (%) Fragment | NA | NA | NA | NA | NA | NA |
| pH | 7.33 | 7.25 | 7.19 | 7.16 | 7.22 | 7.27 |
| Osmolality (mOsmo/kg) | 298 | 297 | 299 | 298 | 300 | 300 |
| Instrumental PM ≥2μm | NA | 14 | NA | 47 | NA | 204 |
| Instrumental PM NMT 25/mL ≥ 10 μm | NA | 1 | NA | 0 | NA | 1 |
| Instrumental PM NMT 3/mL ≥ 25 μm | NA | 0 | NA | 0 | NA | 0 |
| Visual Inspection | Pass | Pass | Pass | Pass | Pass | Pass |

Recombinant Human Insulin (1.0 U/mL) with PBS and KCl Formulation in Glass Ampoules (Sample ID: Glass-PBS-2mM-(KCl-4mM)) and in PL2501 Galaxy Containers (PL2501-PBS-2mM-(KCl-4mM)) at 5±3°C Storage.

FIG. 9B

| Test Description | Units | Tank | Test Intervals in Months | | | | |
|---|---|---|---|---|---|---|---|
| | | | 0 | 1 | 2 | 3 | 6 |
| Visual | N/A | PASS | PASS | PASS | PASS | PASS | PASS |
| pH | N/A | 6.56 | 6.56 | 6.48 | 6.50 | 6.54 | 6.50 |
| PM≥10 μm | counts/mL | NS | 0 | 1 | 1 | 1 | 1 |
| PM≥25 μm | counts/mL | NS | 0 | 0 | 0 | 0 | 0 |
| Assay & Related Substances - Assay | U/mL | 1.05 | 1.00 | 0.99 | 0.99 | 0.97 | 0.93 |
| Assay & Related Substances - Insulin | % area | 100.0 | 100.0 | 97.4 | 94.7 | 94.4 | 90.5 |
| Assay & Related Substances - A21 | % area | NMT 0.5 | NMT 0.5 | 1.3 | 3.0 | 3.5 | 7.6 |
| Assay & Related Substances - Individual R.S. | % area | NMT 0.5 | NMT 0.5 | 0.6 | 0.6 | 0.5 | 0.7 |
| HMWP - Dimer | % area | NMT 1.0 | NMT 1.0 | NMT 1.0 | NMT 1.0 | NMT 1.0 | NMT 1.0 |
| Osmolality | mOsm/kg | 294 | 294 | NA | | 296 | 296 |

Experimental test results for formulation 124 T 65 (pH 6.5) at 25 °C Storage.

FIG. 10

| Test Description | Units | Tank | Test Intervals in Months ||||| 
|---|---|---|---|---|---|---|---|
| | | | 0 | 1 | 2 | 3 | 6 |
| Visual | N/A | PASS | PASS | PASS | PASS | PASS | PASS |
| pH | N/A | 6.80 | 6.80 | 6.73 | 6.78 | 6.79 | 6.75 |
| PM≥10 μm | counts/mL | NS | 0 | 0 | 1 | 1 | 0 |
| PM≥25 μm | counts/mL | NS | 0 | 0 | 0 | 0 | 0 |
| Assay & Related Substances - Assay | U/mL | 1.04 | 1.01 | 0.99 | 0.98 | 0.94 | 0.93 |
| Assay & Related Substances - Insulin | % area | 100.0 | 100.0 | 97.0 | 94.2 | 93.4 | 89.4 |
| Assay & Related Substances - Desamido A21 | % area | NMT 0.5 | NMT 0.5 | 1.6 | 3.4 | 4.2 | 8.7 |
| Assay & Related Substances - Individual R.S. | % area | NMT 0.5 | NMT 0.5 | 0.6 | 0.6 | 0.5 | 0.7 |
| HMWP - Dimer | % area | NMT 1.0 | NMT 1.0 | NMT 1.0 | NMT 1.0 | NMT 1.0 | NMT 1.0 |
| Osmolality | mOsm/kg | 294 | 294 | NA || 296 | 297 |

Experimental test results for formulation 124 T 65 (pH 6.5) at 25 °C Storage.

FIG. 11

| Test Description | Units | Tank | Test Intervals in Months | | | | |
|---|---|---|---|---|---|---|---|
| | | | 0 | 1 | 2 | 3 | 6 |
| Visual | N/A | 1 white fiber | PASS | PASS | PASS | PASS | PASS |
| pH | N/A | 6.98 | 6.98 | 6.90 | 6.94 | 6.96 | 6.90 |
| PM≥10 µm | counts/mL | NS | 0 | 0 | 1 | 1 | 1 |
| PM≥25 µm | counts/mL | NS | 0 | 0 | 0 | 0 | 0 |
| Assay & Related Substances - Assay | U/mL | 1.04 | 1.01 | 1.00 | 0.97 | 0.95 | 0.93 |
| Assay & Related Substances - Insulin | % area | 100.0 | 100 | 96.8 | 94.0 | 93.0 | 88.5 |
| Assay & Related Substances - Desamido A21 | % area | NMT 0.5 | NMT 0.5 | 1.7 | 3.5 | 4.5 | 9.0 |
| Assay & Related Substances - Individual R.S. | % area | NMT 0.5 | NMT 0.5 | 0.6 | 0.5 | 0.6 | NMT 1.0 |
| HMWP - Dimer | % area | NMT 1.0 | NMT 1.0 | NMT 1.0 | NMT 1.0 | NMT 1.0 | NMT 1.0 |
| Osmolality | mOsm/kg | 294 | 295 | NA | | 296 | 297 |

Experimental test results for formulation 124 T 68 (pH 7.0) at 25 °C Storage

FIG. 12

| Test Description | Units | Tank | Test Intervals in Months | | | | |
|---|---|---|---|---|---|---|---|
| | | | 0 | 1 | 2 | 3 | 6 |
| Visual | N/A | PASS | PASS | PASS | PASS | PASS | PASS |
| pH | N/A | 7.19 | 7.20 | 7.12 | 7.16 | 7.18 | 7.13 |
| PM≥10 μm | counts/mL | NS | 1 | 1 | 1 | 1 | 0 |
| PM≥25 μm | counts/mL | NS | 0 | 0 | 0 | 0 | 0 |
| Assay & Related Substances - Assay | U/mL | 1.04 | 100.1 | 0.99 | 0.97 | 0.94 | 0.92 |
| Assay & Related Substances - Insulin | % area | 100.0 | 100.0 | 96.7 | 94.0 | 92.7 | 88.7 |
| Assay & Related Substances - Desamido A21 | % area | NMT 0.5 | NMT 0.5 | 1.8 | 3.5 | 4.5 | 9.0 |
| Assay & Related Substances - Individual R.S. | % area | NMT 0.5 | NMT 0.5 | 0.6 | 0.6 | 0.6 | NMT 0.5 |
| HMWP - Dimer | % area | NMT 1.0 | NMT 1.0 | NMT 1.0 | NMT 1.0 | NMT 1.0 | NMT 1.0 |
| Osmolality | mOsm/kg | 294 | 295 | NA | | 297 | 298 |

Experimental test results for formulation 124 T 72 (pH 7.2) at 25 °C Storage

FIG. 13

| Test Description | Units | Tank | Test Intervals in Months ||||||||| 
|---|---|---|---|---|---|---|---|---|---|---|---|
| | | | 0 | 1 | 2 | 3 | 6 | 9 | 12 | 18 | 24 |
| Visual | N/A | PASS | PASS | PASS | PASS | PASS | PASS | PASS | PASS | PASS | PASS |
| pH | N/A | 6.56 | 6.56 | 6.50 | 6.54 | 6.55 | 6.53 | 6.51 | 6.54 | 6.53 | 6.54 |
| PM≥10 μm | counts/mL | NS | 0 | 0 | 1 | 1 | 0 | 1 | 0 | 0 | 1 |
| PM≥25 μm | counts/mL | NS | 0 | 0 | 0 | 0 | 0 | 0 | 0 | 0 | 0 |
| Assay & Related Substances - Assay | U/mL | 1.05 | 1.00 | 1.00 | 0.98 | 1.00 | 1.01 | 0.94 | 1.0 | 0.99 | 1.0 |
| Assay & Related Substances - Insulin | % area | 100 | 100 | 100 | 100 | 100 | 100 | 99.5 | 99.3 | NA ||
| Assay & Related Substances - Desamido A21 | % area | NMT 0.5 | NMT 0.5 | NMT 0.5 | NMT 0.5 | NMT 0.5 | NMT 0.5 | 0.5 | 0.7 | 0.66 | 0.80 |
| Assay & Related Substances - Individual R.S. | % area | NMT 0.5 | NMT 0.5 | NMT 0.5 | NMT 0.5 | NMT 0.5 | NMT 0.5 | NMT 0.5 | NMT 0.5 | NMT 0.5 | 0.46 |
| HMWP - Dimer | % area | NMT 1.0 | NMT 1.0 | NMT 1.0 | NMT 1.0 | NMT 1.0 | NMT 1.0 | NMT 1.0 | NMT 1.0 | NMT 1.0 | <1.1 |
| Osmolality | mOsm/kg | 294 | 294 | NA || 295 | 295 | NA | 295 | NA | 295 |

Experimental test results for formulation 124 T 65 (pH 6.5) at 5 °C Storage.

FIG. 14

| Test Description | Units | Tank | Test Intervals in Months ||||||||| 
|---|---|---|---|---|---|---|---|---|---|---|---|
| | | | 0 | 1 | 2 | 3 | 6 | 9 | 12 | 18 | 24 |
| Visual | N/A | PASS | PASS | PASS | PASS | PASS | PASS | PASS | PASS | PASS | PASS |
| pH | N/A | 6.80 | 6.8 | 6.75 | 6.79 | 6.80 | 6.77 | 6.78 | 6.78 | 6.79 | 6.79 |
| PM≥10 μm | counts/mL | NS | 0 | 1 | 0 | 0 | 0 | 1 | 0 | 0 | 0 |
| PM≥25 μm | counts/mL | NS | 0 | 0 | 0 | 0 | 0 | 0 | 0 | 0 | 0 |
| Assay & Related Substances - Assay | U/mL | 1.04 | 1.01 | 0.98 | 0.99 | 1.00 | 1.01 | 0.96 | 0.99 | 0.98 | 0.99 |
| Assay & Related Substances - Insulin | % area | 100.0 | 100.0 | 100.0 | 100.0 | 100.0 | 100.0 | 98.5 | 98.6 | NA | NA |
| Assay & Related Substances - Desamido A21 | % area | NMT 0.5 | NMT 0.5 | NMT 0.5 | NMT 0.5 | NMT 0.5 | NMT 0.5 | 0.7 | 0.7 | 0.63 | 0.77 |
| Assay & Related Substances - Individual R.S. | % area | NMT 0.5 | NMT 0.5 | NMT 0.5 | NMT 0.5 | NMT 0.5 | NMT 0.5 | NMT 0.5 | NMT 0.5 | 0.5 | 0.53 |
| HMWP - Dimer | % area | NMT 1.0 | NMT 1.0 | NMT 1.0 | NMT 1.0 | NMT 1.0 | NMT 1.0 | NMT 1.0 | NMT 1.0 | NMT 1.0 | <1.1 |
| Osmolality | mOsm/kg | 294 | 294 | NA | NA | 295 | 295 | NA | 295 | NA | 296 |

Experimental test results for formulation 124 T 68 (pH 6.8) at 5 °C Storage.

FIG. 15

| Test Description | Units | Tank | Test Intervals in Months ||||||||| 
|---|---|---|---|---|---|---|---|---|---|---|---|
| | | | 0 | 1 | 2 | 3 | 6 | 9 | 12 | 18 | 24 |
| Visual | N/A | 1 white fiber | PASS | PASS | PASS | PASS | PASS | PASS | PASS | PASS | PASS |
| pH | N/A | 6.98 | 6.98 | 6.91 | 6.96 | 6.96 | 6.91 | 6.95 | 6.95 | 6.95 | 6.95 |
| PM≥10 μm | counts/mL | NS | 0 | 0 | 1 | 0 | 0 | 0 | 0 | 0 | 0 |
| PM≥25 μm | counts/mL | NS | 0 | 0 | 0 | 0 | 0 | 0 | 0 | 0 | 0 |
| Assay & Related Substances - Assay | U/mL | 1.04 | 1.01 | 1.01 | 1.01 | 1.00 | 1.01 | 0.94 | 0.99 | 0.99 | 1.00 |
| Assay & Related Substances - Insulin | % area | 100.0 | 100.0 | 100.0 | 100.0 | 100.0 | 100.0 | 99.1 | 98.3 | NA ||
| Assay & Related Substances - Desamido A21 | % area | NMT 0.5 | NMT 0.5 | NMT 0.5 | NMT 0.5 | NMT 0.5 | NMT 0.5 | 0.9 | 0.7 | 0.64 | 0.72 |
| Assay & Related Substances - Individual R.S. | % area | NMT 0.5 | NMT 0.5 | NMT 0.5 | NMT 0.5 | NMT 0.5 | NMT 0.5 | NMT 0.5 | NMT 0.5 | 0.51 | 0.46 |
| HMWP - Dimer | % area | NMT 1.0 | NMT 1.0 | NMT 1.0 | NMT 1.0 | NMT 1.0 | NMT 1.0 | NMT 1.0 | NMT 1.0 | NMT 1.0 | <1.1 |
| Osmolality | mOsm/kg | 294 | 295 | NA || 296 | 296 | NA | 295 | NA | 296 |

Experimental test results for formulation 124 T 70 (pH 7.0) at 5 °C Storage.

FIG. 16

| Test Description | Units | Tank | Test Intervals in Months ||||||||| 
|---|---|---|---|---|---|---|---|---|---|---|---|
| | | | 0 | 1 | 2 | 3 | 6 | 9 | 12 | 18 | 24 |
| Visual | N/A | PASS | PASS | PASS | PASS | PASS | PASS | PASS | PASS | PASS | PASS |
| pH | N/A | 7.19 | 7.2 | 7.14 | 7.18 | 7.18 | 7.15 | 7.19 | 7.16 | 7.16 | 7.16 |
| PM≥10 μm | counts/mL | NS | 1 | 0 | 0 | 1 | 0 | 0 | 0 | 0 | 0 |
| PM≥25 μm | counts/mL | NS | 0 | 0 | 0 | 0 | 0 | 0 | 0 | 0 | 0 |
| Assay & Related Substances - Assay | U/mL | 1.04 | 1.01 | 1.02 | 1.01 | 0.99 | 1.00 | 0.94 | 0.99 | 0.98 | 0.99 |
| Assay & Related Substances - Insulin | % area | 100.0 | 100.0 | 100.0 | 100.0 | 100.0 | 100.0 | 98.4 | 98.6 | NA | NA |
| Assay & Related Substances - Desamido A21 | % area | NMT 0.5 | NMT 0.5 | NMT 0.5 | NMT 0.5 | NMT 0.5 | NMT 0.5 | 1.0 | 0.6 | 0.5 | 0.69 |
| Assay & Related Substances - Individual R.S. | % area | NMT 0.5 | NMT 0.5 | NMT 0.5 | NMT 0.5 | NMT 0.5 | NMT 0.5 | 0.6 | NMT 0.5 | 0.55 | 0.50 |
| HMWP - Dimer | % area | NMT 1.0 | NMT 1.0 | NMT 1.0 | NMT 1.0 | NMT 1.0 | NMT 1.0 | NMT 1.0 | NMT 1.0 | NMT 1.0 | <1.1 |
| Osmolality | mOsm/kg | 294 | 295 | NA | NA | 297 | 297 | NA | 296 | NA | 297 |

Experimental test results for formulation 124 T 72 (pH 7.2) at 5 °C Storage.

FIG. 17

Example 3:

| Sample Condition | Insulin Concentration (U/mL) |
|---|---|
| No foam | 0.95 |
| Foam | 0.94 |
| More Foam | 0.91 |

The Effect of Foaming on Insulin Concentration for Test Solution: 3000 mL Insulin Formulation

FIG. 18

| Assay Parameter | Portion 1 (no foam) | Portion 2 (with foam) | Portion 3 (after foam) |
|---|---|---|---|
| Total Insulin (U/mL) | 0.96 | 0.94 | 0.97 |
| Total Desamido (% area) | 1.48 | 1.35 | 1.56 |
| Other (% area) | LT 0.25 | LT 0.25 | LT 0.25 |

Test Solution: 600 mL Insulin Formulation.

FIG. 19

Example 4:

| Container Type | Unit # | Insulin in Baxter Formulation | |
|---|---|---|---|
| | | Total Insulin (U/mL) | Total Insulin (% of Tank) |
| Tank Sample | N/A | 0.994 | 100.0 |
| Glass | Mean | 1.003 | 100.9 |
| Container 1 | Mean | 0.982 | 98.8 |
| Container 2 | Mean | 0.978 | 98.4 |
| Container 3 | Mean | 0.974 | 98.0 |
| Container 4 | Mean | 0.962 | 96.8 |
| Container 5 | Mean | 0.986 | 99.2 |
| Container 6 | Mean | 0.999 | 100.5 |
| Container 7 | Mean | 0.962 | 96.8 |

Summary of Assay Results for Baxter Premix Insulin Injection, 1.0 U/mL in different plastic containers.

FIG. 20

| Container Type | Unit # | Insulin in Baxter Formulation, Albumin Spiked | |
|---|---|---|---|
| | | Total Insulin (U/mL) | Total Insulin (% of Tank) |
| Tank Sample | N/A | 1.000 | 100.0 |
| Glass | Mean | 1.005 | 100.5 |
| Container 1 | Mean | 1.013 | 101.3 |
| Container 2 | Mean | 1.018 | 101.8 |
| Container 3 | Mean | 1.010 | 101.0 |
| Container 4 | Mean | 1.001 | 100.1 |
| Container 5 | Mean | 0.993 | 99.3 |
| Container 6 | Mean | 1.004 | 100.4 |
| Container 7 | Mean | 0.996 | 99.6 |

Summary of Assay Results for Baxter Premix Insulin Injection, 1 U/mL (spiked with 1 mg/mL Albumin).

FIG. 21

| Container Type | Unit # | Premix Insulin Injection, 1 U/mL | Premix Insulin Injection, 1U/mL (spiked with 1 mg/mL Albumin) |
|---|---|---|---|
| | | Total Insulin (U/mL) | |
| | Tank Sample | 0.994 | 1.000 |
| Container 1 | Average (n = 3) | 0.982 | 1.013 |
| Container 2 | Average (n = 3) | 0.978 | 1.018 |
| Container 3 | Average (n = 3) | 0.974 | 1.010 |
| Container 4 | Average (n = 3) | 0.962 | 1.001 |
| Container 5 | Average (n = 3) | 0.986 | 0.993 |
| Container 6 | Average (n = 3) | 0.999 | 1.004 |
| Container 7 | Average (n = 3) | 0.962 | 0.996 |
| Glass | Average (n = 3) | 1.003 | 1.005 |

Insulin assay results

FIG. 22

Insulin loss at pH of 6.5 for insulin premix formulations with different excipients.

Insulin loss at pH of 7.75 for insulin premix formulations with different excipients.

Insulin loss at pH of 9.0 for insulin premix formulations with different excipients.

Example 5.

| Solution ID | Phosphate Ratio (monobasic:dibasic) (mM) | Measured pH After Phosphate Addition |
|---|---|---|
| #1-1 | 2.1:2.9 | 6.77 |
| #1-2 | 2.2:2.8 | 6.75 |
| #1-3 | 2.3:2.7 | 6.70 |
| #1-4 | 2.4:2.6 | 6.67 |
| #1-5 | 2.5:2.5 | 6.64 |
| #1-6 | 2.6:2.4 | 6.61 | pH values of the solution after the addition of the phosphate buffering agents.

FIG. 26

| Solution ID | Phosphate Ratio (monobasic:dibasic) (mM) | pH Average | Difference between Average pH & Target pH (6.8) |
|---|---|---|---|
| Control - No Phosphate | N/A | 3.16 | -3.64 |
| Sample 1 | 1.1:3.9 | 6.87 | +0.07 |
| Sample 2 | 1.125:3.875 | 6.87 | +0.07 |
| Sample 3 | 1.15:3.85 | 6.84 | +0.04 |
| Sample 4 | 1.175:3.825 | 6.79 | -0.01 |

Differences between experimental average pH and target pH.

FIG. 27

Example 6.

|  | Grid Search | Surface Crawl 1 | Surface Crawl 2 | Surface Crawl 3 |
|---|---|---|---|---|
| pH | 6.50 | 6.50 | 6.64 | 6.50 |
| Arg (mM) | 0.0 | 2.4 | 3.7 | 5.6 |
| Lys (mM) | 10.0 | 8.0 | 7.2 | 10.0 |
| Gly (mM) | 8.0 | 6.3 | 6.8 | 5.6 |
| Optimized Result (Low/High Limits) | 100.21% (96.48/103.94) | 98.76% (94.98/102.53) | 98.28% (94.60/101.96) | 98.59% (94.89/102.30) |

Surface Crawls for the "Assay % Initial" Parameter (25 °C Model).

FIG. 28

|  | Grid Search | Surface Crawl 1 | Surface Crawl 2 | Surface Crawl 3 |
|---|---|---|---|---|
| pH | 7.00 | 6.80 | 6.82 | 6.90 |
| Arg (mM) | 10.0 | 7.7 | 7.5 | 5.7 |
| Lys (mM) | 5.0 | 6.2 | 5.4 | 6.4 |
| Gly (mM) | 10.0 | 9.6 | 9.9 | 9.8 |
| Optimized Result (Low/High Limits) | 1.18% (-2.06/4.43) | 1.46% (-1.65/4.58) | 1.40% (-1.73/4.54) | 1.49% (-1.62/4.60) |

Surface Crawls for the "Change in A21" Parameter (25 °C Model).

FIG. 29

|  | Grid Search | Surface Crawl 1 | Surface Crawl 2 | Surface Crawl 3 | Nominal |
|---|---|---|---|---|---|
| pH | 6.50 | 6.50 | 6.50 | 6.64 | 7.4 |
| Arg (mM) | 0.0 mM | 7.5 mM | 10.0 mM | 9.2 mM | 5 mM |
| Lys (mM) | 10.0 mM | 10.0 mM | 5.0 mM | 7.3 mM | 0 |
| Gly (mM) | 10.0 mM | 7.5 mM | 0.0 mM | 9.9 mM | 0 |
| Optimized Assay Initial (Low/High Limits) | 99.86% (96.23/103.48) | 98.48% (94.94/102.02) | 95.68% (92.21/99.14) | 97.17% (93.88/100.46) | 91.44% (88.05/94.82) |
| Change in A21 (Low/High Limits) | 1.72% (-1.69/5.14) | 2.52% (-0.81/5.85) | 2.25% (-1.02/5.51) | 1.49% (-1.61/4.59) | 3.42% (0.24/6.61) |

Combined Response Optimization at 25 °C vs. Nominal Formulation (25 °C Model)

FIG. 31

| Parameter | Total Insulin | Rel Sub (%) | | pH | HMWP (%) | | | |
|---|---|---|---|---|---|---|---|---|
| | U/mL | A21 | Total | | Monomer | Dimer | Aggregate | Fragment |
| Time 0 - Plastic | 0.99 | 0.3 | 0.4 | 7.05 | N/A | N/A | N/A | N/A |
| Time 0 - Glass | 0.98 | 0.3 | 0.4 | 7.05 | 99.92 | 0.08 | ND | ND |
| 3Month - Plastic | 0.978 | 0.572 | 0.572 | 7.01 | 99.83 | 0.17 | N/A | N/A |
| 3Month - Glass | 0.987 | 0.620 | 0.620 | 7.02 | 99.85 | 0.15 | ND | ND |
| 6Month - Plastic | 0.978 | 0.552 | 0.735 | 7.04 | 99.85 | 0.15 | N/A | N/A |
| 6Month - Glass | 0.993 | 0.605 | 0.902 | 7.01 | 99.87 | 0.13 | ND | ND |
| 12Month - Plastic | 0.959 | 1.73 | 1.93 | 7.05 | 99.828 | 0.172 | N/A | N/A |
| 12Month - Glass | 0.980 | 1.74 | 1.88 | 7.05 | 99.863 | 0.137 | ND | ND |
| 18Month - Plastic | 0.969 | 1.65 | 2.76 | 6.99 | 99.91 | 0.09 | N/A | N/A |
| 18Month - Glass | 0.978 | 1.70 | 3.10 | 7.02 | 99.92 | 0.08 | ND | ND |
| 23Month - Plastic | 0.958 | 1.92 | 3.49 | 7.04 | 99.82 | 0.18 | N/A | N/A |
| 23Month - Glass | 0.965 | 1.97 | 3.32 | 7.05 | 99.91 | 0.09 | ND | ND |

Data for Formulation 1 at 5 °C Storage (5 mM Phosphate, 2 mM Arginine, pH 7.0).

FIG. 32

| Parameter | Total Insulin | Rel Sub (%) | | pH | HMWP (%) | | | |
|---|---|---|---|---|---|---|---|---|
| | U/mL | A21 | Total | | Monomer | Dimer | Aggregate | Fragment |
| Time 0 - Plastic | 0.95 | 0.3 | 0.5 | 7.42 | 100 | N/A | N/A | N/A |
| Time 0 - Glass | 0.97 | 0.3 | 0.4 | 7.42 | 100 | ND | ND | ND |
| 3Month - Plastic | 0.941 | 0.666 | 0.666 | 7.35 | 99.83 | 0.17 | ND | N/A |
| 3Month - Glass | 0.977 | 0.678 | 0.678 | 7.40 | 99.79 | 0.21 | ND | ND |
| 6Month - Plastic | 0.943 | 0.667 | 0.850 | 7.35 | 99.84 | 0.16 | N/A | N/A |
| 6Month - Glass | 0.971 | 0.733 | 0.811 | 7.34 | 99.86 | 0.14 | ND | ND |
| 12Month - Plastic | 0.915 | 1.89 | 2.07 | 7.40 | 99.827 | 0.173 | N/A | N/A |
| 12Month - Glass | 0.946 | 2.01 | 2.01 | 7.47 | 99.782 | 0.218 | ND | ND |
| 18Month - Plastic | 0.928 | 1.93 | 3.12 | 7.34 | 99.93 | 0.07 | N/A | N/A |
| 18Month - Glass | 0.933 | 1.95 | 3.22 | 7.40 | 99.86 | 0.14 | ND | ND |
| 23Month - Plastic | 0.913 | 2.19 | 3.69 | 7.38 | 99.79 | 0.21 | N/A | N/A |
| 23Month - Glass | 0.943 | 2.34 | 4.01 | 7.47 | 99.86 | 0.14 | ND | ND |

Data for Formulation 2 at 5 °C Storage (5 mM Phosphate, 2 mM Arginine, pH 7.4).

FIG. 33

| Parameter | Total Insulin | Rel Sub (%) | | pH | HMWP (%) | | | |
|---|---|---|---|---|---|---|---|---|
| | U/mL | A21 | Total | | Monomer | Dimer | Aggregate | Fragment |
| Time 0 - Plastic | 0.95 | 0.3 | 0.5 | 7.75 | N/A | N/A | N/A | N/A |
| Time 0 - Glass | 0.89 | 0.2 | 0.4 | 7.72 | 100.00 | ND | ND | ND |
| 3Month - Plastic | 0.943 | 0.754 | 0.754 | 7.65 | 99.81 | 0.19 | ND | ND |
| 3Month - Glass | 0.871 | 0.726 | 0.726 | 7.68 | 99.81 | 0.19 | ND | ND |
| 6Month - Plastic | 0.953 | 0.717 | 0.892 | 7.61 | 99.86 | 0.14 | N/A | N/A |
| 6Month - Glass | 0.909 | 0.749 | 0.856 | 7.59 | 99.84 | 0.16 | ND | ND |
| 12Month - Plastic | 0.937 | 1.93 | 2.12 | 7.69 | 99.81 | 0.189 | N/A | N/A |
| 12Month - Glass | 0.888 | 2.06 | 2.06 | 7.81 | 99.82 | 0.177 | ND | ND |
| 18Month - Plastic | 0.943 | 2.00 | 3.20 | 7.61 | 99.92 | 0.08 | N/A | N/A |
| 18Month - Glass | 0.859 | 2.00 | 3.46 | 7.73 | 99.87 | 0.13 | ND | ND |
| 23Month - Plastic | 0.924 | 2.24 | 3.78 | 7.64 | 99.82 | 0.18 | N/A | N/A |
| 23Month - Glass | 0.862 | 2.24 | 4.05 | 7.82 | 99.87 | 0.13 | ND | ND |

Data for Formulation 3 at 5 °C Storage (5 mM Phosphate, 2 mM Arginine, pH 7.8).

FIG. 34

| Parameter | Total Insulin | Rel Sub (%) | | pH | HMWP (%) | | | |
|---|---|---|---|---|---|---|---|---|
| | U/mL | A21 | Total | | Monomer | Dimer | Aggregate | Fragment |
| Time 0 - Plastic | 0.99 | 0.3 | 0.4 | 7.05 | 100 | N/A | N/A | N/A |
| Time 0 - Glass | 0.98 | 0.3 | 0.4 | 7.05 | 99.92 | 0.08 | ND | ND |
| 1Month - Plastic | 0.929 | 0.576 | 2.102 | 7.04 | 99.68 | 0.10 | ND | 0.22 |
| 1Month - Glass | 0.964 | 0.849 | 1.876 | 7.06 | 99.68 | ND | ND | 0.32 |
| 3Month - Plastic | 0.918 | 5.297 | 8.691 | 7.03 | 99.46 | 0.23 | ND | 0.32 |
| 3Month - Glass | 0.969 | 5.342 | 8.665 | 7.02 | 99.37 | 0.28 | ND | 0.35 |
| 6Month - Plastic | 0.887 | 8.937 | 15.299 | 7.03 | 99.20 | 0.33 | N/A | 0.47 |
| 6Month - Glass | 0.885 | 9.047 | 14.454 | 7.03 | 99.30 | 0.21 | ND | 0.49 |

Data for Formulation 1 at 25 °C Storage (5 mM Phosphate, 2 mM Arginine, pH 7.0).

FIG. 35

| Parameter | Total Insulin | Rel Sub (%) | | pH | HMWP (%) | | | |
|---|---|---|---|---|---|---|---|---|
| | U/mL | A21 | Total | | Monomer | Dimer | Aggregate | Fragment |
| Time 0 - Plastic | 0.95 | 0.3 | 0.5 | 7.42 | N/A | N/A | N/A | N/A |
| Time 0 - Glass | 0.97 | 0.3 | 0.4 | 7.42 | 100.00 | N/D | ND | ND |
| 1Month - Plastic | 0.911 | 0.634 | 1.752 | 7.4 | 99.64 | 0.08 | ND | 0.28 |
| 1Month - Glass | 0.917 | 0.882 | 2.081 | 7.40 | 99.66 | ND | ND | 0.34 |
| 3Month - Plastic | 0.894 | 5.156 | 8.530 | 7.35 | 99.24 | 0.19 | ND | 0.57 |
| 3Month - Glass | 0.939 | 5.395 | 8.781 | 7.40 | 99.06 | 0.23 | ND | 0.71 |
| 6Month - Plastic | 0.846 | 8.458 | 15.472 | 7.34 | 98.80 | 0.22 | N/A | 0.98 |
| 6Month - Glass | 0.872 | 8.475 | 15.146 | 7.36 | 98.59 | 0.19 | ND | 1.22 |

Data for Formulation 2 at 25 °C Storage (5 mM Phosphate, 2 mM Arginine, pH 7.4).

FIG. 36

| Parameter | Total Insulin | Rel Sub (%) | | pH | HMWP (%) | | | |
|---|---|---|---|---|---|---|---|---|
| | U/mL | A21 | Total | | Monomer | Dimer | Aggregate | Fragment |
| Time 0 - Plastic | 0.95 | 0.3 | 0.5 | 7.75 | N/A | N/A | N/A | N/A |
| Time 0 - Glass | 0.89 | 0.2 | 0.4 | 7.72 | 100.00 | ND | ND | ND |
| 1Month - Plastic | 0.913 | 0.697 | 2.328 | 7.68 | 99.51 | 0.07 | ND | 0.42 |
| 1Month - Glass | 0.861 | 0.946 | 2.485 | 7.72 | 99.66 | ND | ND | 0.34 |
| 3Month - Plastic | 0.894 | 5.003 | 8.242 | 7.63 | 98.85 | 0.18 | ND | 0.97 |
| 3Month - Glass | 0.836 | 5.222 | 8.445 | 7.71 | 98.48 | 0.24 | ND | 1.28 |
| 6Month - Plastic | 0.835 | 8.082 | 16.219 | 7.58 | 97.99 | 0.18 | N/A | 1.83 |
| 6Month - Glass | 0.742 | 7.797 | 16.204 | 7.60 | 97.59 | 0.19 | ND | 2.23 |

N/A = Not Applicable; ND = None Detected; Rel Sub = Related Substances

Data for Formulation 3 at 25 °C Storage (5 mM Phosphate, 2 mM Arginine, pH 7.8)

FIG. 37

| Parameters | | Arginine 0 mM | | Arginine 1 mM | | Arginine 2 mM | | Arginine 5 mM | |
|---|---|---|---|---|---|---|---|---|---|
| Time | | Time 0 | 23M-5C | Time 0 | 23M-5C | Time 0 | 23M-5C | Time 0 | 23M-5C |
| pH | | 7.41 | 7.36 | 7.37 | 7.32 | 7.37 | 7.28 | 7.45 | 7.42 |
| Assay U/mL | | 0.97 | 0.94 | 0.98 | 0.953 | 0.95 | 0.929 | 0.94 | 0.93 |
| Rel Sub (%) | A-21 (%) | 0.3 | 2.17 | 0.2 | 2.15 | 0.2 | 1.88 | 0.2 | 2.23 |
| | Total | 0.8 | 4.1 | 0.5 | 3.66 | 0.5 | 3.43 | 0.5 | 3.86 |
| HMWP (%) | Monomer | 100 | 99.64 | 100 | 99.8 | 100 | 99.85 | 100 | 99.87 |
| | Dimer | ND | 0.36 | ND | 0.2 | ND | 0.15 | ND | 0.13 |
| | Aggregate | ND | ND | ND | ND | ND | ND | ND | ND |
| | Fragment | ND | ND | ND | ND | ND | ND | ND | ND |

The long term stability over storage at 5 °C for 23 months for formulations having different concentrations of arginine at pH 7.4.

FIG. 38

| Parameters | | Arginine 0 mM | | Arginine 1 mM | | Arginine 2 mM | | Arginine 5 mM | |
|---|---|---|---|---|---|---|---|---|---|
| Time | | Time 0 | 6M-25C | Time 0 | 6M-25C | Time 0 | 6M-25C | Time 0 | 6M-25C |
| pH | | 7.41 | 7.32 | 7.37 | 7.28 | 7.37 | 7.19 | 7.45 | 7.35 |
| Assay U/mL | | 0.97 | 0.851 | 0.98 | 0.882 | 0.95 | 0.867 | 0.94 | 0.843 |
| Rel Sub (%) | A-21 (%) | 0.3 | 8.31 | 0.2 | 8.49 | 0.2 | 7.31 | 0.2 | 8.47 |
| | Total | 0.8 | 16.21 | 0.5 | 15.85 | 0.5 | 13.62 | 0.5 | 15.37 |
| HMWP (%) | Monomer | 100 | 98.67 | 100 | 98.9 | 100 | 98.87 | 100 | 98.82 |
| | Dimer | ND | 0.48 | ND | 0.28 | ND | 0.21 | ND | 0.16 |
| | Aggregate | ND | ND | ND | ND | ND | ND | ND | ND |
| | Fragment | ND | 0.85 | ND | 0.82 | ND | 0.91 | ND | 1.02 |

The long term stability over storage at 25 °C for 6 months for formulations having different concentrations of arginine at pH 7.4.

FIG. 39

| Lot No. | Parameters | Tank Release | Time 0 | 24M-5 C | 24M-5C +30D-25C |
|---|---|---|---|---|---|
| 1 | pH | | 6.8 | 6.9 | 6.9 |
| | % Assay Insulin | 101.0 | 100.0 | 98.2 | 97.8 |
| | A-21 Desamido | | 0.64 | 1.40 | 1.17 |
| | Any Rel Sub | | ND | 0.34 | 0.31 |
| | Total Rel Subs | | ND | 0.91 | 1.01 |
| 2 | pH | | 6.8 | 6.8 | 6.9 |
| | % Assay Insulin | 104.0 | 100.3 | 98.0 | 97.7 |
| | A-21 Desamido | | 0.58 | 1.19 | 1.11 |
| | Any Rel Sub | | ND | 0.31 | 0.32 |
| | Total Rel Subs | | ND | 0.97 | 1.02 |
| 3 | pH | | 6.8 | 6.9 | 6.9 |
| | % Assay Insulin | 99.0 | 100.3 | 98.3 | 97.7 |
| | A-21 Desamido | | 0.57 | 1.22 | 1.13 |
| | Any Rel Sub | | ND | 0.28 | 0.27 |
| | Total Rel Subs | | ND | 0.67 | 0.94 |
| 4 | pH | | 6.8 | 6.8 | 6.8 |
| | % Assay Insulin | 98.0 | 96.3 | 96.1 | 93.5 |
| | A-21 Desamido | | 0.75 | 0.96 | 1.11 |
| | Any Rel Sub | | ND | ND | 0.29 |
| | Total Rel Subs | | ND | ND | 0.53 |

Long-term stability of the insulin premix formulations through the shelf life of the formulations, namely 24 months storage at a refrigeration temperature of 2 °C to 8 °C plus 30 days storage at room temperature of 22 °C to 28 °C.

FIG. 40

SEQUENCE LISTING

```
<160> NUMBER OF SEQ ID NOS: 2

<210> SEQ ID NO 1
<211> LENGTH: 21
<212> TYPE: PRT
<213> ORGANISM: Homo sapiens

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 30
<212> TYPE: PRT
<213> ORGANISM: Homo sapiens

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30
```

INSULIN PREMIX FORMULATION AND PRODUCT, METHODS OF PREPARING SAME, AND METHODS OF USING SAME

PRIORITY CLAIM

This application is a continuation of U.S. application Ser. No. 16/681,392, filed Nov. 12, 2019, entitled "INSULIN PREMIX FORMULATION AND PRODUCT, METHODS OF PREPARING SAME, AND METHODS OF USING SAME", which claims priority to and the benefit of U.S. Provisional Patent Application Ser. No. 62/843,881, filed May 6, 2019, entitled "INSULIN PREMIX FORMULATION AND PRODUCT, METHODS OF PREPARING SAME, AND METHODS OF USING SAME" and U.S. Provisional Patent Application Ser. No. 62/862,573, filed Jun. 17, 2019, entitled "INSULIN PREMIX FORMULATION AND PRODUCT, METHODS OF PREPARING SAME, AND METHODS OF USING SAME," the entire contents of each of which are hereby incorporated by reference and relied upon.

SEQUENCE LISTINGS

The instant application contains Sequence Listings which have been filed electronically in ASCII format and are hereby incorporated by reference in its entirety. Said ASCII copy, created on Mar. 10, 2020, is named 3712044-05805_SL.txt and is 894 bytes in size.

TECHNICAL FIELD

The present disclosure generally relates to a pharmaceutically acceptable insulin premix formulation containing about 0.1 Unit/mL to about 10.0 Unit/mL of insulin with a low concentration of A-21 desamido insulin impurity. The present disclosure also relates to methods of making and using such insulin premix formulation. The pharmaceutically acceptable insulin premix formulation may be aseptically filled into a container, preferably a flexible container, to form a sterile pharmaceutical insulin premix product. The insulin premix product can be a single use premix which is a sterile, stable and ready to use aqueous solution for intravenous (IV) administration such as intravenous infusion. The present disclosure also relates to methods of making and using such insulin premix product.

BACKGROUND

Insulin is the primary polypeptide hormone produced by beta cells of the pancreatic islets of an individual. Insulin is responsible for controlling the cellular uptake, utilization and storage of glucose, amino acids and fatty acids while inhibiting the breakdown of glycogen, protein and fat. Human insulin has the empirical formula $C_{257}H_{383}N_{65}O_{77}S_6$, a molecular weight of about 5808 Da and an isoelectric point (pI) of about 5.3. It is a dimer of an A-chain of 21 amino acids (SEQ ID NO: 1) and a B-chain of 30 amino acids (SEQ ID NO: 2), which are linked together by disulphide bonds. The sequence of the human insulin is shown in FIG. 1.

In a healthy individual, the basal glucose level tends to remain constant. The secretion of insulin by the individual pancreas is strictly coupled to the blood glucose level. Therefore, the blood glucose and insulin levels are modulated to minimize changes in glucose concentration while relatively normal production and utilization of glucose are maintained.

However, in an individual with metabolic disorders such as diabetes mellitus, the individual may have reduced ability or absolutely no ability to produce insulin, or have insulin resistance. Therefore, glycemic control using insulin is fundamental to the management of blood glucose level for the individual with diabetes mellitus.

Furthermore, in a critically ill individual in an intensive care unit (ICU) even with no history of diabetes mellitus, insulin administration is critical to manage hyperglycemia, a common finding caused by insulin resistance in the liver and the muscle tissue of the individual. The insulin resistance is generally considered to be an adaptive response to stresses resulting from surgery, trauma or sepsis in order to provide glucose for the brain, the red blood cells and the wound healing. Severe harmful medical consequences can happen if the blood glucose level of an ICU patient is not controlled, such as temporary and permanent patient harm, prolonged hospitalization, the need for medical intervention and even patient death. For example, the 2005 USP MedMarx Annual Report reported a serious harmful medical error relating to insulin. A patient was admitted to hospital to have a kidney transplant. An insulin infusion was ordered and started pre-operatively. Post-operation, the patient was received to the ICU without insulin infusion. The patient's blood glucose rose to 443 mg/dL with other significant electrolyte abnormalities documented, which caused the patient a lengthened ICU stay with dialysis reinstituted.

Therefore, it is now a common practice in hospitals to administer insulin intravenously to every ICU patient to stabilize the blood glucose level between about 80-150 mg/dL. After the blood glucose level is stabilized, a maintenance dosing of insulin is often administered.

Insulin can be administered intravenously to a patient only under medical supervision at a low concentration, such as about 0.01-10.0 Unit/mL, titrated at a rate calculated per the insulin sliding scale guideline to control the blood glucose level of the patients, including the ICU patients. The dosage shall be individualized based on the patent's metabolic needs, blood glucose monitoring results and glycemic control goal.

With the ever increasingly large number of Americans having diabetes mellitus and large number of ICU patients, insulin is one of the most widely used drugs in hospitals. However, there is a long history of medication errors associated with the administration of insulin in hospitals, especially administration by intravenous (IV) infusion. In 2007, the USP MedMarx Annual Report showed that insulin was the product involved in the highest number of medication errors in the calendar year 2005, and also the highest number of harmful medical errors representing more than 11% of all reported harmful medication errors.

One of the major factors contributing to the insulin medical errors is the wrong dosage of insulin during dispensing or administering insulin in hospitals. Currently, different types and brands of concentrated insulin commercial products are available on the market at different concentrations, such as 100 Unit/mL, 200 Unit/mL, and 500 Unit/mL. However, there is no single usage, sterile, stable and ready to use IV infusion system with insulin at about 0.01-10.0 Unit/mL available. The IV infusion system with insulin at about 0.01-10.0 Unit/mL has to be prepared in the hospitals by diluting the concentrated insulin commercial products with tonicity adjuster solution. This often involves preparing an IV infusion system by transferring insulin from a small volume vial container into a flexible plastic container holding the tonicity adjuster solution or diluent, right before starting the infusion to patients. Furthermore, this preparation is stable for only about 24-48 hours at room temperature. Medical errors occur in this preparation process due to miscommunication, using the wrong type of insulin, measurement errors, cross contamination and insulin degradation due to exposure to light, air and high temperature. This practice of in-hospital preparation of IV infusion system of insulin largely contributes to the insulin medical errors, such as wrong dosages or wrong types of insulin. Due to the large amount of reported insulin medical errors, the insulin administration guideline recommends that all the IV infusion systems with insulin at 0.01-10.0 Unit/mL (or U/mL) must be prepared in the pharmacy.

Therefore, there is a need for a single usage, sterile, stable and ready to use premix product with insulin at 0.1-10.0 U/mL for IV infusion.

Furthermore, according to the Handbook on Injectable Drugs (20th Edition, ASHP's Guide to IV Compatibility and Stability, page 768), the adsorption of insulin to the surface of intravenous infusion solution containers, such as glass and plastic (including polyvinyl chloride (PVC), ethylene vinyl acetate (EVA), polyethylene (PE) and other polyolefins), tubing and filters has been demonstrated. Estimates of the loss range up to about 80% for the entire infusion apparatus, although varying results using differing test methods, equipment, and procedures have been reported. Estimates of adsorption of around 20% to 30% are common.

According to the Handbook on Injectable Drugs (20th Edition, ASHP's Guide to IV Compatibility and Stability), different approaches were attempted in the past to reduce the adsorption of insulin. One approach is to add albumin human to infusion solutions. However, the degree to which albumin human prevents adsorption is uncertain. Other additives such as vitamins, electrolytes, and drugs were also suggested to have a similar effect. Other recommended approaches in avoiding or minimizing adsorption include adding a small amount of the patient's blood to the insulin solution and storing or flushing the administration apparatus with the insulin solution to saturate the IV infusion set prior to administration.

However, according to the Handbook on Injectable Drugs (20th Edition, ASHP's Guide to IV Compatibility and Stability), whether one attempts to prevent insulin adsorption loss or not, it does not appear to be possible to add an amount of insulin to an infusion solution and know precisely what portion of that amount will actually be given to the patient. Monitoring the patient's response to therapy and making the appropriate adjustments on the basis of that response are, therefore, of prime importance.

Therefore, there is a need to prepare a single usage, sterile, stable and ready to use premix product with insulin at 0.1-10.0 U/mL for IV infusion which does not adsorb or absorb to the IV infusion flexible container.

SUMMARY

Applicant has prepared a pharmaceutically acceptable insulin premix formulation containing about 0.1 Unit/mL to about 10.0 Unit/mL of insulin with a low concentration of A-21 desamido insulin impurity. For example, the insulin premix formulation may have less than about 5.0%, and more preferably less than about 4.0% of A-21 desamido insulin impurity by weight of total insulin, measured using a suitable reverse-phase high performance liquid chromatography (HPLC) or UHPLC method such as is provided in the USP insulin monographs; adjusted for use with low concentration insulin preparations.

The insulin premix formulation may further comprise at least one tonicity adjuster and at least one buffer. The insulin premix formulation is isosmotic with an individual's body fluids or blood. The osmolality of the formulation is preferably in the isosmotic range of an individual's body fluids or blood of about 280 to about 320 mOsmo/kg. The present disclosure also relates to methods of making and using such insulin premix formulation. The pharmaceutically acceptable insulin premix formulation may be aseptically filled into a flexible container to form a pharmaceutical insulin premix product. The insulin premix product can be a single usage premix which is a sterile, stable and ready to use aqueous solution for intravenous administration such as intravenous infusion. The present disclosure also relates to methods of making and using such insulin premix product. For example, the insulin premix product can be used for glycemic control in an individual with metabolic disorders, such as an individual with diabetes mellitus, or an individual in intensive care unit (ICU) that has been prescribed insulin.

Applicant found that the insulin premix product is unexpectedly stable when freshly prepared and also during its shelf-life of storage at a refrigeration temperature of 2° C. to 8° C. for 24 months followed by additional 30 days at room temperature (23° C.-27° C.), even without any added preservative, any added zinc, any added surfactant or any other added stabilizing excipient. Applicant did not add any zinc, any preservative or any surfactant into the insulin premix product. In contrast, the concentrated insulin commercial products currently available on the market have added zinc, added preservative and added glycerol/glycerin/glycerine. One of the concentrated insulin commercial products has zinc in amount of 21 µg/mL, meta-cresol in amount of 3 mg/mL and glycerin 16 mg/mL per its package insert. On the contrary, the insulin premix product disclosed herein has essentially no meta-cresol, glycerol or added zinc. The zinc content of the insulin premix product was measured to be 0.13-0.16 µg/mL which came from the raw material of insulin and is significantly lower than that of the commercial products.

The insulin premix formulation and product preferably have a pH value of about 6.5-7.2, and more preferably of about 6.6-7.0. The pH value of the insulin premix is stabilized at 6.5-7.2 through the end of its shelf life.

Applicant found that the insulin premix formulation has unexpectedly low concentration of A-21 desamido insulin impurity when freshly prepared and also through the end of its shelf life. The insulin premix product is further essentially free of or has very low concentration of insulin dimer, hexamer or any other high molecular weight protein (HMWP) when freshly prepared and through the end of its shelf life. The total concentration of insulin dimer, hexamer or any other high molecular weight protein (HMWP) is preferably no more than about 4.0%, no more than about 3.0%, no more than 2.0%, more preferably no more than about 1.7%, or even no more than 1.1% by weight of the total insulin, measured using a suitable size exclusion chromatography (SEC) method such as is provided in the USP insulin monographs; adjusted for use with low concentration insulin preparations.

Applicant further found that the insulin in the premix product unexpectedly does not stick to common flexible containers, which minimizes the loss of insulin due to adsorption or absorption to flexible containers and thus significantly improves the accuracy of the insulin dosage for administration.

Furthermore, the insulin premix product as disclosed and prepared herein is a single usage premix and is ready to be administered intravenously to an individual in need thereof without requiring further dilution. Therefore, the insulin premix product disclosed herein eliminates the necessity to prepare an insulin IV infusion system having insulin at a concentration of 0.1-10.0 Unit/mL diluted from the concentrated insulin commercial products in the pharmacy or in hospitals right before the starting of insulin IV infusion. Consequently, the insulin premix product would significantly reduce medical errors in dispensing and administrating insulin and dramatically improve safety and efficiency in using insulin in hospitals nationally.

BRIEF DESCRIPTION OF THE DRAWINGS

FIG. 1 shows the sequence of the human insulin with an A-chain of 21 amino acids (SEQ ID NO: 1) and a B-chain of 30 amino acids (SEQ ID NO: 2).

FIG. 2 shows the characteristics of the flexible plastic containers for insulin premix products disclosed herein.

FIGS. 4, 5, 6, 7A, 7B, 8A, 8B, 9A and 9B show the test results of the experimental study in Example 1 disclosed herein. FIG. 4 shows the insulin concentration changes for insulin (1.0 Unit/mL) with PBS (phosphate buffer) formulation in glass ampoules (Sample ID: Glass-PBS-2 mM) and in PL2501 GALAXY® container (Sample ID: PL2501-PBS-2 mM) at 5±3° C. and 25±2° C. for up to 25.5 months (110 weeks) and at 40±2° C. for up to 24 weeks. FIG. 5 shows the insulin concentration changes for insulin (1.0 Unit/mL) with Arginine formulation in glass ampoules (Sample ID: Glass-Arginine-2 mM) and in PL2501 GALAXY® container (Sample ID: PL2501-Arginine-2 mM) at 53° C. and 252° C. for up to 25.5 months (110 weeks) and at 402° C. for up to 24 weeks. FIG. 6 shows the insulin concentration changes for insulin (1.0 Unit/mL) with PBS (phosphate buffer plus KCl) formulation in glass ampoules (Sample ID: Glass-PBS-2 mM-(KCl-4 mM)) and in PL2501 GALAXY® container (Sample ID: PL2501-PBS-2 mM-(KCl-4 mM)) at 53° C. and 252° C. for up to 25.5 months (110 weeks) and at 402° C. for up to 24 weeks. FIGS. 7A and 7B show the experimental results of the Recombinant Human Insulin (1.0 U/mL) with PBS (Phosphate Buffer) Formulation in Glass Ampoules (Sample ID: Glass-PBS-2 mM) and in PL2501 Galaxy Containers (PL2501-PBS-2 mM) at 5±3° C. Storage. FIGS. 8A and 8B show the experimental results of the Recombinant Human Insulin (1.0 U/mL) with Arginine Formulation in Glass Ampoules (Sample ID: Glass-Arginine-2 mM) and in PL2501 Galaxy Containers (PL2501-Arginine-2 mM) at 5±3° C. Storage. FIGS. 9A and 9B show the experimental results of the Recombinant Human Insulin (1.0 U/mL) with PBS and KCl Formulation in Glass Ampoules (Sample ID: Glass-PBS-2 mM-(KCl-4 mM)) and in PL2501 Galaxy Containers PL2501-PBS-2 mM-(KCl-4 mM)) at 5±3° C. Storage.

FIGS. 10-17 show the test results of the experimental study in Example 2 disclosed herein.

FIGS. 18-19 show the test results of the experimental study in Example 3 disclosed herein.

FIGS. 20-25 show the test results of the experimental study in Example 4 disclosed herein.

FIGS. 26-27 show the test results of the experimental study in Example 5 disclosed herein.

FIG. 28-40 shows the test results of the experimental study in Example 6 disclosed herein.

FIG. 41 shows a reverse-phase HPLC chromatogram showing the separation of insulin and the A-21 desamido insulin impurity and the peak area of the A-21 desamido insulin impurity for quantification of its content for one of the insulin premix formulation samples. This image is provided for illustrative purpose only. It will be understood to those skilled in the art that the peak retention times may shift when different HPLC systems, columns, mobile phase separations, etc. are used.

DETAILED DESCRIPTION

Definitions

Figure 3:
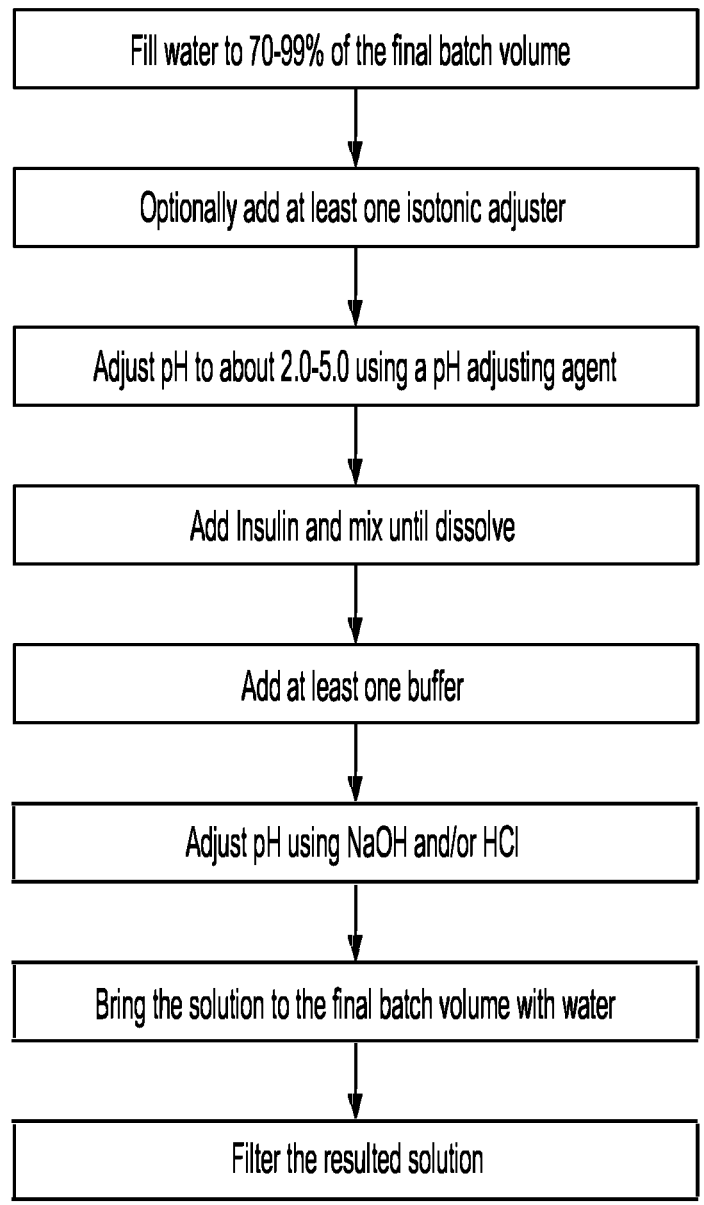
FIG. 3 is a flowchart of a non-limiting example of an embodiment of a method of making a pharmaceutically acceptable insulin premix formulation according to the present disclosure.
Figure 4:
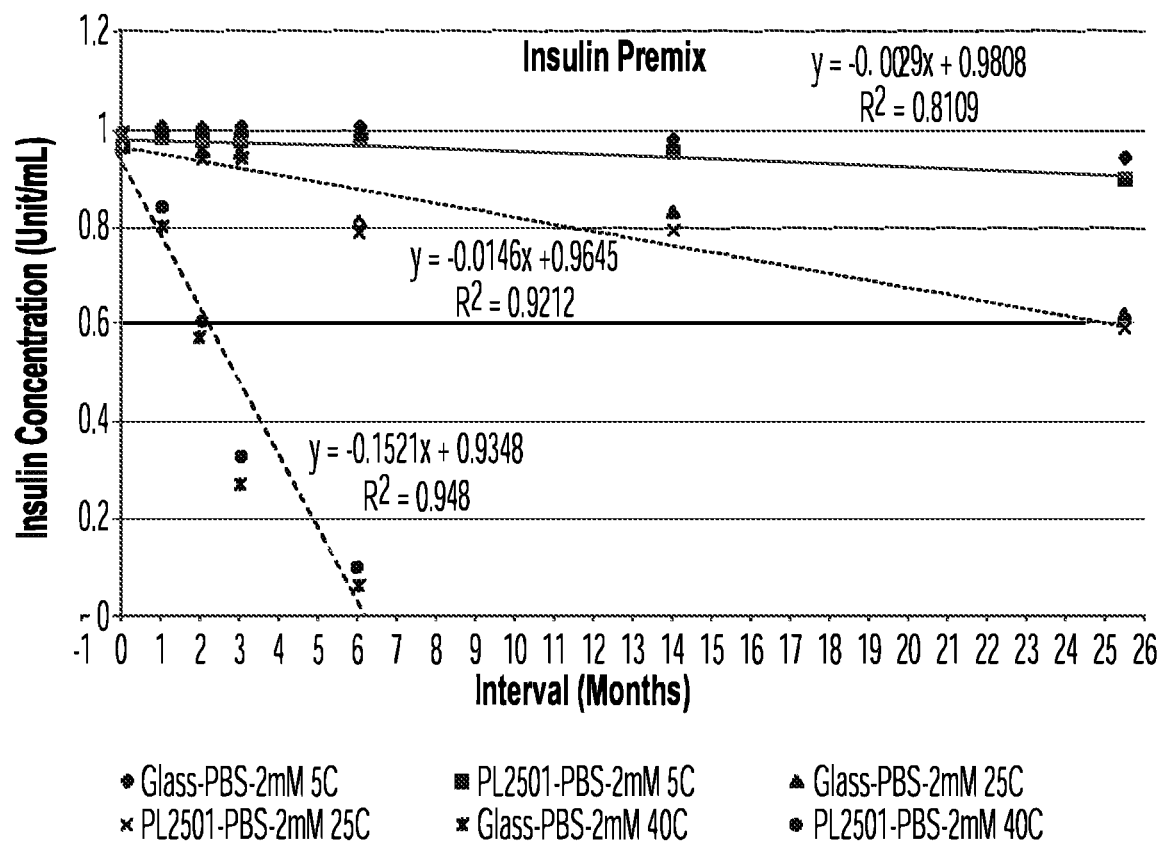
Figure 5:
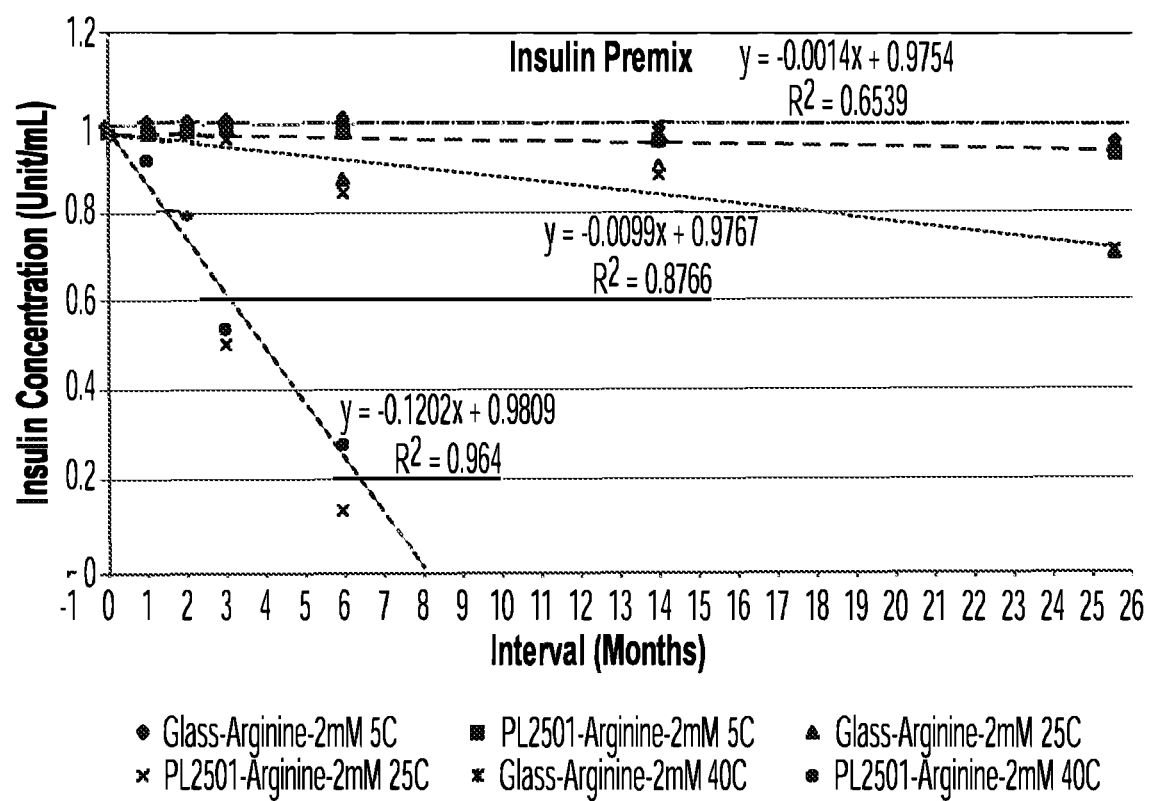

Some definitions are provided hereafter. Nevertheless, definitions may be located in the "Embodiments" section below, and the above header "Definitions" does not mean that such disclosures in the "Embodiments" section are not definitions.

As used in this disclosure and the appended claims, the term "premix" is a ready to use aqueous solution suitable for direct administration to patients, including IV infusion, without requiring further dilution. Preferably, the premix solution is supplied as a sterile solution, and is stable over its shelf life as described herein.

As used in this disclosure and the appended claims, the term "sterile" is understood to mean free from any bacteria or other living microorganisms.

As used in this disclosure and the appended claims, the term "isosmotic" is understood to mean having the same osmolality as an individual's body fluids or blood, typically from about 280 to about 320 mOsm/kg.

As used in this disclosure and the appended claims, the term "freshly prepared" is understood to mean within 30 days after a sample is manufactured, while the sample is stored at a refrigeration temperature of 2° C. to 8° C.

As used in this disclosure and the appended claims, the term "insulin premix product is stable" is understood to mean that the insulin concentration is within 10% of the original concentration when freshly prepared, the A-21 desamido insulin impurity is less than about 4.0% by weight of the total insulin as measured by reverse-phase HPLC, the high molecular weight protein (HMWP) content is less than about 2.0% by weight of the total insulin as measured by SEC, and pH is within about 6.5-7.2.

As used in this disclosure and the appended claims, the term "shelf-life" of insulin premix formulation or product is understood to mean 24 months stored at refrigeration temperatures of 2° C. to 8° C. followed by 30 days stored at room temperatures of 23° C. to 27° C. with substantially no exposure to light during the entire storage period.

As used in this disclosure and the appended claims, the terms "glycerol," "glycerin" and "glycerine" are interchangeable.

Non-limiting examples of insulin suitable for the disclosure herein include a human insulin, a recombinant human insulin, a human insulin analog, an insulin derivative, an active insulin metabolite or combinations thereof.

As used in this disclosure and the appended claims, "recombinant human insulin" is structurally identical to native human insulin and is produced by recombinant DNA technology. In one embodiment, the recombinant human insulin is manufactured by the Microbial Synthesis approach. In another embodiment, the recombinant human insulin is manufactured by recombinant DNA technology, utilizing *Pichia pastoris* (yeast) as the production organism.

As used in this disclosure and the appended claims, "insulin analog" is an analog of naturally occurring insulins, namely human insulin or animal insulins, which differ by substitution of at least one naturally occurring amino acid residue with other amino acid residues and/or addition or removal of at least one amino acid residue from the corresponding, otherwise identical, naturally occurring insulin. The added and/or replaced amino acid residues can also be those which do not occur naturally.

As used in this disclosure and the appended claims, "tonicity adjuster" is an excipient added to injectable preparations to prevent osmotic shock at the site of injection upon administration, and thereby reduce local irritation. Typical excipients used for tonicity adjustment include saline, glycerin, mannitol, dextrose and trehalose. Tonicity is a colligative property that depends primarily on the number of dissolved particles in solution. Hence, the amount of the tonicity adjuster to be added depends on the specific formulation. Typically, osmolality of 280 to 320 mOsm/kg is considered iso-osmotic.

All percentages expressed herein are by weight of the total weight of the composition unless expressed otherwise. When reference herein is made to the pH, values correspond to pH measured at about 25° C. with standard equipment.

As used herein, "about," "approximately" and "substantially" are understood to refer to numbers in a range of numerals, for example the range of −10% to +10% of the referenced number, preferably −5% to +5% of the referenced number, more preferably −1% to +1% of the referenced number, most preferably −0.1% to +0.1% of the referenced number.

All numerical ranges herein should be understood to include all integers, whole or fractions, within the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

As used in this disclosure and the appended claims, the singular forms "a," "an" and "the" include plural referents unless the context clearly dictates otherwise. Thus, for example, reference to "a component" or "the component" includes two or more components.

The words "comprise," "comprises" and "comprising" are to be interpreted inclusively rather than exclusively. Likewise, the terms "include," "including," "containing" and "having" should all be construed to be inclusive, unless such a construction is clearly prohibited from the context. Further in this regard, these terms specify the presence of the stated features but not preclude the presence of additional or further features.

Nevertheless, the compositions and methods disclosed herein may lack any element that is not specifically disclosed herein. Thus, a disclosure of an embodiment using the term "comprising" is (i) a disclosure of embodiments having the identified components or steps and also additional components or steps, (ii) a disclosure of embodiments "consisting essentially of" the identified components or steps, and (iii) a disclosure of embodiments "consisting of" the identified components or steps. Any embodiment disclosed herein can be combined with any other embodiment disclosed herein.

The term "and/or" used in the context of "X and/or Y" should be interpreted as "X," or "Y," or "X and Y." Similarly, "at least one of X or Y" should be interpreted as "X," or "Y," or "X and Y." For example, "at least one of monobasic sodium phosphate or dibasic sodium phosphate" should be interpreted as "monobasic sodium phosphate," or "dibasic sodium phosphate," or "both monobasic sodium phosphate and dibasic sodium phosphate."

Where used herein, the terms "example" and "such as," particularly when followed by a listing of terms, are merely exemplary and illustrative and should not be deemed to be exclusive or comprehensive.

A "subject" or "individual" is a mammal, preferably a human. As used herein, an "effective amount" is an amount that prevents a deficiency, treats a disease or medical condition in an individual, or, more generally, reduces symptoms, manages progression of the disease, or provides a nutritional, physiological, or medical benefit to the individual.

The terms "treatment" and "treat" include both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a diagnosed pathologic condition or disorder; and treatment of patients at risk of contracting a disease or suspected to have contracted a disease, as well as patients who are ill or have been diagnosed as suffering from a disease or medical condition. The terms "treatment" and "treat" do not necessarily imply that a subject is treated until total recovery. The terms "treatment" and "treat" also refer to the maintenance and/or promotion of health in an individual not suffering from a disease but who may be susceptible to the development of an unhealthy condition. The terms "treatment" and "treat" are also intended to include the potentiation or otherwise enhancement of one or more primary prophylactic or therapeutic measures. As non-limiting examples, a treatment can be performed by a patient, a caregiver, a doctor, a nurse, or another healthcare professional.

The term "unit dosage form", as used herein, refers to physically discrete units suitable as unitary dosages for human and animal subjects, each unit containing a predetermined quantity of the composition disclosed herein in amount sufficient to produce the desired effect, in association with a pharmaceutically acceptable diluent, carrier or vehicle. The specifications for the unit dosage form depend on the particular compounds employed, the effect to be achieved, and the pharmacodynamics associated with each compound in the host.

The term "mM", as used herein, refers to a molar concentration unit of an aqueous solution, which is mmol/L. For example, 1.0 mM equals 1.0 mmol/L.

The term "pharmaceutically acceptable" as used herein refers to substances that do not cause substantial adverse allergic or immunological reactions when administered to a subject.

The terms "substantially no," "essentially free" or "substantially free" as used in reference to a particular component means that any of the component present constitutes less than about 3.0% by weight, such as less than about 2.0% by weight, less than about 1.0% by weight, preferably less than about 0.5% by weight or, more preferably, less than about 0.1% by weight.

EMBODIMENTS

The present disclosure generally relates to a pharmaceutically acceptable insulin premix formulation which comprises about 0.1-10.0 U/mL of insulin. The insulin premix formulation is an aqueous solution that may be aseptically filled into a flexible container to form a pharmaceutically acceptable insulin premix product. The insulin premix product is preferably a sterile, stable and ready to use aqueous solution. The insulin premix product is preferably a single usage product. The insulin premix product is preferably clear and colourless. The insulin product can be administered to an individual in need thereof for improved therapy of glycemic control. The individual may be a mammal, preferably a human including adults and children. The individual may be an individual with metabolic disorders, including an individual in an intensive care unit (ICU) or an individual having diabetes mellitus such as Type I and Type II diabetes.

An aspect of the present disclosure is a pharmaceutically acceptable insulin premix formulation. Non-limiting examples of the pharmaceutically acceptable insulin premix formulations may comprise insulin in a concentration of about 0.1-10.0 U/mL, preferably about 0.5-5.0 U/mL, more preferably about 0.5-2.0 U/mL, and most preferably about 1.0 U/mL by volume of the formulation. The concentration of insulin in the premix formulations as disclosed herein is preferably the final concentration for direct administration to patients, which preferably does not require any further dilution by or addition of any extra ingredient which is not already in the insulin premix formulation.

Non-limiting examples of the insulin may include a human insulin, a recombinant human insulin, a human insulin analog, an insulin derivative, an active insulin metabolite or combinations thereof. Non-limiting examples of the pharmaceutically acceptable insulin premix formulation may comprise water to form an aqueous solution.

Non-limiting examples of the insulin premix formulation may be stable when freshly prepared and preferably has a shelf-life of 24 months stored at refrigeration temperatures of 2° C. to 8° C. followed by 30 days stored at room temperatures of 23° C. to 27° C. with substantially no exposure to light over the entire storage period.

Non-limiting examples of the pharmaceutically acceptable insulin premix formulation may preferably have a pH value of about 6.5-7.2, more preferably about 6.6-7.0, and most preferably about 6.8 when freshly prepared and through the end of its shelf life. Applicant found that the pH value of the insulin premix formulations is one of the major factors impacting the stability of the formulations. Applicant found that the insulin premix formulations with a pH value of about 6.5-7.2, preferably about 6.6-7.0 as disclosed herein demonstrate unexpectedly high stability when freshly prepared and during its shelf life stored in either a flexible container or a glass container. Furthermore, Applicant found that the published pH range (about 7.0-7.8) in the USP monograph for concentrated insulin products such as 100.0 U/mL insulin is not the preferred pH range for the insulin premix formulations at low insulin concentration, such as about 0.1-10.0 U/mL. Although the pH ranges for the two different concentration products overlap, the ideal pH for the insulin premix formulation (about 0.1-10.0 U/mL insulin) is preferably lower than that of the concentrated insulin solution (100.0 U/mL) marketed products.

Non-limiting examples of the insulin premix formulation preferably have low concentrations of impurities. For example, the insulin premix formulation has less than about 8.0%, preferably less than about 5.0%, more preferably less than about 4.0% of A-21 desamido insulin impurity by weight of total insulin when freshly prepared and through the end of its shelf life. The A-21 desamido insulin impurity may be less than about 5.0%, preferably less than about 4.0%, more preferably less than about 3.0%, most preferably less than about 2.5%, or even less than 2.0% by weight of total insulin in the insulin premix formulation when freshly prepared. The amount of A-21 desamido insulin impurity is measured using a suitable reverse-phase HPLC or UHPLC method such as is provided in the USP insulin monographs; adjusted for use with low concentration insulin preparations. It will be understood to those skilled in the art, the weight percentage of the A-21 desamido insulin impurity can be calculated based on the percentage of the peak area of the A-21 desamido insulin impurity in relation to the total insulin peak areas of the HPLC chromatograms.

Non-limiting examples of the insulin premix formulation may be preferably essentially free of or has very low concentration of insulin dimer, hexamer or any other high molecular weight protein (HMWP) when freshly prepared and at the end of its shelf life. In one embodiment, the total amount of insulin dimer, hexamer and any other HMWP is less than about 4.0%, less than about 3.0%, preferably less than about 2.0%, most preferably less than about 1.7%, or even less than about 1.1% by weight of the total insulin when freshly prepared and at the end of its shelf life. The total amount of the insulin dimer, hexamer or any other HMWP is measured using a suitable size exclusion chromatography (SEC) method such as is provided in the USP insulin monographs; adjusted for use with low concentration insulin preparations.

Non-limiting examples of the insulin premix formulation preferably have more than about 90%, preferably more than about 95%, more preferably more than about 98%, and most preferably more than about 99% insulin in monomer form by weight of the total insulin when freshly prepared and at the end of its shelf life with substantially no exposure to light.

Non-limiting examples of the insulin premix formulation preferably have low concentrations of each individual unknown related substance. In one embodiment, the insulin premix formulation has less than about 5.0%, preferably less than about 4.0%, more preferably less than about 3.0% of the total unknown related substances by weight of the total insulin when freshly prepared and over its shelf life. The total unknown related substances is preferably less than about 2.0%, or even less than about 1.5% by weight of the total insulin when freshly prepared measured by reverse-phase HPLC. The insulin premix formulation is preferably essentially free of any visible particles.

Non-limiting examples of the pharmaceutically acceptable insulin premix formulation may further comprise at least one tonicity adjuster. The at least one tonicity adjuster may be one or both of sodium chloride (NaCl) and dextrose. In one embodiment, the at least one tonicity adjuster is preferably sodium chloride. The concentration of sodium chloride is preferably about 0.8%-1.0%, more preferably about 0.855%-0.945%, most preferably about 0.9% by weight of the total formulation. In another embodiment, the at least one tonicity adjuster is preferably dextrose. The concentration of dextrose is preferably about 4.0%-11.0%. In one embodiment, the at least one tonicity adjuster is preferably about 5.0% dextrose by weight of the formulation. In yet another embodiment, the at least one tonicity adjuster is preferably about 5.51% dextrose by weight of the formulation. In yet another embodiment, the at least one tonicity adjuster is preferably about 10.0% dextrose by weight of the formulation.

Non-limiting examples of the pharmaceutically acceptable insulin premix formulation may further comprise at least one buffer. The at least one buffer is preferably selected from the group consisting of monobasic sodium phosphate (monohydrate), dibasic sodium phosphate (anhydrous), tribasic sodium phosphate, citrate, histidine, phosphate, tryptophan, maleate, carbonate and mixtures thereof.

Non-limiting examples of the concentration of the at least one buffer is at a concentration of about 0.1-50.0 mM, preferably about 1.0-10.0 mM, more preferably about 3.0-7.0 mM, and most preferably about 5.0 mM by total volume of the formulation.

Non-limiting examples of the at least one buffer is preferably a combination of monobasic sodium phosphate and dibasic sodium phosphate. The molar ratio of monobasic sodium phosphate to dibasic sodium phosphate may be about 1:0.1 to about 1:10, preferably about 1:1 to about 1:5, more preferably about 1:1 to about 1:4. In one embodiment, the molar ratio of monobasic sodium phosphate to dibasic sodium phosphate is about 2.1:2.9. In another embodiment, the molar ratio of monobasic sodium phosphate to dibasic sodium phosphate is about 1:3.44.

Non-limiting examples of the pharmaceutically acceptable insulin premix formulation may further comprise one or more of an amino acid, such as arginine, glycine and lysine; and one or more of potassium salt, such as potassium chloride. The concentration of each of the excipients in the insulin premix formulation is about 0.1 mM to about 10.0 mM, preferably about 1.0 mM to about 5.0 mM by volume of the formulation.

Non-limiting examples of the pharmaceutically acceptable insulin premix formulation may further comprise a sacrificial protein, such as albumin, in an amount of about 0.1-10.0 mg/mL, preferably about 0.5-5.0 mg/mL, and more preferably of about 0.5-2.0 mg/mL by volume of the formulation.

Non-limiting examples of the pharmaceutically acceptable insulin premix formulation may contain one or more of a preservative, such as phenol, cresol, meta-cresol, sorbates, parabens and any other added preservative suitable for intravenous administration.

Preferably the pharmaceutically acceptable insulin premix formulation contains substantially no added phenol, cresol, meta-cresol, parabens or any other added preservative.

Non-limiting examples of the pharmaceutically acceptable insulin premix formulation may contain one or more of a surfactant, such as polyethylene glycerols, alkyl carboxylates-fatty acid salts, sodium lauryl sulfate, sodium dodecyl sulphate, phosphatidylcholine (lecithin), polysorbates, sorbitan monolaurate and any other surfactant suitable for intravenous administration.

Preferably the pharmaceutically acceptable insulin premix formulation contains substantially no any added surfactant.

Non-limiting examples of the pharmaceutically acceptable insulin premix formulation may contain one or more of an antioxidant, such as vitamin E, vitamin C, butylatedhydroxyanisole (BHA), butylatedhydroxytoluene (BHT), sulfites and any other antioxidant suitable for intravenous administration.

Preferably the pharmaceutically acceptable insulin premix formulation contains substantially no any added antioxidant.

Non-limiting examples of the pharmaceutically acceptable insulin premix formulation may contain added zinc. Preferably, the pharmaceutically acceptable insulin premix formulation contains less than about 0.30 µg/mL, preferably less than about 0.21 µg/mL, and more preferably less than 0.16 µg/mL of zinc of the formulation.

Non-limiting examples of the pharmaceutically acceptable insulin premix formulation preferably contain less than 0.21 µg/mL of zinc.

Non-limiting examples of the pharmaceutically acceptable insulin premix formulation preferably contain less than 0.16 µg/mL of zinc.

Non-limiting examples of the pharmaceutically acceptable insulin premix formulation preferably contain substantially no added zinc.

Non-limiting examples of the pharmaceutically acceptable insulin premix formulation preferably contain substantially no zinc.

Non-limiting examples of the pharmaceutically acceptable insulin premix formulation is preferably essentially free of any added zinc, any added preservative, any added glycerol and any added surfactant. Furthermore, Applicant found that the pharmaceutically acceptable insulin premix formulation as disclosed herein is unexpectedly stable over its shelf life (24 months stored at about 5° C. followed by 30 days stored at about 25° C. with substantially no exposure to light over the entire storage time) even without any added zinc, any added preservative, any added glycerol or any added surfactant. In one embodiment, no zinc, preservative, glycerol or surfactant is added to the insulin premix formulation. The content of the zinc in the insulin premix formulation as disclosed and prepared herein may be about 0.13-0.16 µg/mL which comes from the insulin raw material. In contrast, the commercially available concentrated insulin products have added zinc, preservatives (e.g., meta-cresol) and glycerol. For example, one of the concentrated insulin commercial products has zinc in amount of 21 µg/mL, meta-cresol (preservative) in amount of 3 mg/mL and glycerol in amount of 16 mg/mL.

Non-limiting examples of the pharmaceutically acceptable insulin premix formulation may contain glycerol/glycerine/glycerin.

Preferably the pharmaceutically acceptable insulin premix formulation contains substantially no added glycerol/glycerine/glycerin.

Non-limiting examples of the pharmaceutically acceptable insulin premix formulation are unexpectedly stable when freshly prepared and also during its shelf-life of storage at refrigeration temperatures of 2° C. to 8° C. for 24 months followed by additional 30 days at room temperatures of 23° C.-27° C., even without any added preservative, any added antioxidant, any added zinc, any added surfactant or any other added stabilizing excipient. Therefore, the pharmaceutically acceptable insulin premix formulation as disclosed and prepared herein may not require any added preservative, any added antioxidant, any added zinc, any added surfactant or any other added stabilizing excipient. However, in some embodiments, one or more of the excipients, such as preservatives, antioxidants, zinc, surfactants or any other added stabilizing excipients may be added into the insulin premix formulation.

Non-limiting examples of the pharmaceutically acceptable insulin premix formulation preferably do not adsorb or absorb to common flexible containers suitable for IV infusion. Therefore, the insulin premix formulation as disclosed herein may prevent insulin loss due to essentially no or low absorption onto flexible containers for common flexible containers suitable for IV infusion.

Non-limiting examples of the flexible container may be a flexible plastic container having an inner surface contacting the insulin solution, wherein the inner surface may be made of a plastic material, or a layer of plastic material. Preferred plastic materials for the inner surface contacting the insulin solution include polyethylene (PE), linear low density polyethylene (LLDPE), polyvinyl chloride (PVC), polypropylene (PP), copolymer, and modified polymer or copolymer. For example, the inner surface of the flexible container may be made of a flexible PE or LLDPE. The characteristics of non-limiting examples of the inner surface of common flexible containers are described in FIG. 2.

In one embodiment, the flexible container is a 100 ml GALAXY® single dose flexible container intended for intravenous drug infusion, such as GALAXY® PL 2501. The GALAXY® flexible container may be made of a single polymeric layer or multiple layers bonded together, or co-extruded. These film layers can comprise polymers such as, but not limited to, polyolefins, polyethers, and polyamides (nylon, for example). The inner surface of the GALAXY® flexible container is polyethylene (PE) or a layer of PE, which contacts the drug solution inside the bag.

In another embodiment, Applicant found that the insulin premix formulation as disclosed herein unexpectedly does not adsorb or absorb to the inner surface of the flexible containers regardless the types of flexible containers tested with or without the addition of an amino acid such as arginine, lysine, glycine; a sacrificial protein such as albumin; or a potassium salt such as KCl. Therefore, the insulin premix formulation as disclosed herein can significantly reduce insulin loss due to insulin adsorption or absorption to flexible containers and thus cut down medical errors in administration of the insulin to patients in need thereof in hospitals.

In some embodiments, the pharmaceutically acceptable insulin premix formulation may further comprise a pH-adjusting agent, such as sodium hydroxide (NaOH) and hydrochloric acid (HCl).

Another aspect of the present disclosure is a method for manufacturing a pharmaceutically acceptable insulin premix formulation. Non-limiting examples of the method preferably comprise 1) adding insulin to water and mixing until homogenous to form an aqueous solution, wherein the concentration of insulin is about 0.1-10.0 U/mL.

Non-limiting examples of the method for manufacturing the pharmaceutically acceptable insulin premix formulation preferably further comprise adjusting the pH of the aqueous solution to be about 6.5-7.2.

Non-limiting examples of the method for manufacturing the pharmaceutically acceptable insulin premix formulation preferably further comprise adding at least one tonicity adjuster to water and mixing until homogenous.

Non-limiting example of the method for manufacturing the pharmaceutically acceptable insulin premix formulation is preferably the method illustrated in FIG. 3. Although some embodiments of the method include all of the depicted steps, other embodiments of the method omit one or all of the depicted steps, and each step is optional unless indicated otherwise. The present disclosure is not limited to the specific embodiment of the method shown in FIG. 3.

In one embodiment, the method for manufacturing the pharmaceutically acceptable insulin premix formulation, the method comprises: 1) specifying a final volume and filling a container with water to about 70%-99% of the final volume, preferably about 90% of the final volume at room temperature; 2) adjusting pH to about 2.0-5.0 using an acid or an acidic buffering agent; 3) adding insulin and mixing until dissolved in a concentration of about 0.1-10.0 U/mL of the total formulation; 4) testing and adjusting pH to preferably about 6.5-7.2, more preferably about 6.6-7.0, and most preferably about 6.8, if needed using NaOH and/or HCl; 5) bringing the resulted solution to the final volume with water and mixing until homogenous; and 6) sterile-filtering the solution to form the pharmaceutically acceptable insulin premix formulation.

Non-limiting examples of the tonicity adjuster include sodium chloride (NaCl), dextrose and combinations thereof. In one embodiment, the tonicity adjuster is preferably NaCl. The concentration of the NaCl is preferably about 0.8%-1.0%, more preferably about 0.855%-0.945%, and most preferably about 0.9% by weight of the total formulation. In another embodiment, the tonicity adjuster is preferably dextrose, and the concentration of dextrose is about 4.0%-11.0%, for example, about 5.0%, about 5.51% or about 10% by weight of the total formulation.

Non-limiting examples of the method for manufacturing the pharmaceutically acceptable insulin premix formulation preferably further comprise adding at least one buffer and mixing until homogenous. In this regard, some embodiments of the method may not comprise adding a buffer, but preferred embodiments include adding at least one buffer. The concentration of the at least one buffer is preferably about 0.1 mM to about 20.0 mM, preferably about 1.0 mM to about 10.0 mM, more preferably about 3.0 mM to about 7.0 mM, and most preferably about 5.0 mM by the volume of the formulation.

Non-limiting examples of the at least one buffer is selected from the group consisting of monobasic sodium phosphate (monohydrate), dibasic sodium phosphate (anhydrous), tribasic sodium phosphate, citrate, histidine, phosphate, tryptophan, maleate, carbonate and mixtures thereof. Preferably, the at least one buffer is a combination of monobasic sodium phosphate and dibasic sodium phosphate. The molar ratio of total monobasic sodium phosphate to dibasic sodium phosphate is preferably about 1:0.1 to about 1:10, more preferably about 1:1 to about 1:5, and most preferably about 1:1 to 1:4. In one embodiment, the molar ratio of monobasic sodium phosphate to dibasic sodium phosphate is preferably about 2.1:2.9. In another embodiment, the molar ratio of monobasic sodium phosphate to dibasic sodium phosphate is preferably about 1:3.44.

Non-limiting examples of the method for manufacturing the pharmaceutically acceptable insulin premix formulation may preferably involve aseptic manufacturing and container filling and sealing techniques for drug products according to known methods in the art, including but not limited to the passing the aqueous solution through a filter.

Non-limiting examples of the method for manufacturing the pharmaceutically acceptable insulin premix formulation may preferably exclude adding any zinc.

Non-limiting examples of the method for manufacturing the pharmaceutically acceptable insulin premix formulation may preferably exclude adding any preservative, such as phenol, cresol, meta-cresol, parabens or any other added preservative.

Non-limiting examples of the method for manufacturing the pharmaceutically acceptable insulin premix formulation may preferably exclude adding any surfactant.

Non-limiting examples of the method for manufacturing the pharmaceutically acceptable insulin premix formulation preferably exclude adding any glycerol/glycerin/glycerine.

Non-limiting examples of the method for manufacturing the pharmaceutically acceptable insulin premix formulation preferably exclude adding zinc, adding any preservative, adding any surfactant, or adding glycerol. Furthermore, Applicant found that the pharmaceutically acceptable insulin premix formulation as disclosed herein is unexpectedly stable for 24 months stored at about 5° C. followed by 30 days stored at about 25° C. with substantially no exposure to light, even without any added zinc, any added preservative, any added glycerol or any added surfactant. In contrast, the commercially available concentrated insulin products currently available on the market have added zinc, preservatives (e.g. meta-cresol) and glycerol. For example, one of the concentrated insulin commercial products has zinc in amount of 21 µg/mL, meta-cresol (preservative) in amount of 3 mg/mL and glycerol in amount of 16 mg/mL.

Non-limiting examples of the method for manufacturing the pharmaceutically acceptable insulin premix formulation preferably use hydrochloric acid (HCl) as the acid to adjust the pH value of the aqueous solution.

Non-limiting examples of the method for manufacturing the pharmaceutically acceptable insulin premix formulation preferably use monobasic sodium phosphate as the acidic buffering agent to adjust the pH of the aqueous solution.

In one embodiment, the method for manufacturing the pharmaceutically acceptable insulin premix formulation use monobasic sodium phosphate as the acidic buffering agent to adjust pH of the aqueous solution to about 2.0-5.0 before adding insulin, as illustrated in FIG. 3. Applicant found that the addition and mixing sequence of different ingredients in the method illustrated in FIG. 3 can reduce mixing time, ensure complete and fast dissolution of insulin, minimize the pH adjustment using NaOH and/or HCl and reduce the formation of impurities such as desamido insulin impurities without negatively impacting the stability of the insulin. Insulin has higher solubility and dissolves faster in acidic aqueous solution. Furthermore, insulin is unstable in pH basic aqueous solution. Therefore, the aqueous solution is preferably first adjusted to lower the pH value of the solution to about 2.0-5.0 and thus to ensure the complete and fast dissolution of insulin. Therefore, the addition and mixing sequence disclosed herein can reduce the mixing time, ensure the stability of the insulin and reduce the formation of impurities.

At least a portion of these steps in the method for manufacturing the pharmaceutically acceptable insulin premix formulation as illustrated in FIG. 3 may optionally be performed at about 2-8° C., for example approximately 5° C. or, additionally or alternatively, at ambient conditions, i.e., a temperature of about 25° C. and a pressure of about 1.0 atm. Preferably, the mixing is performed with constant low speed agitation for some or all of the steps of mixing to minimize foaming. Preferably, each ingredient is mixed until completely homogenous before adding the next ingredient.

Further in this regard, the low speed agitation together with the specified mixing sequence disclosed above minimize foam formation during the mixing and thus prevent insulin trapping in the foam, and therefore achieve an improved accuracy of the insulin concentrations in the insulin premix formulations.

Non-limiting examples of the method for manufacturing the pharmaceutically acceptable insulin premix formulation preferably further comprise storing the insulin premix formulation in a container, for example for a time period up to about 24 months at a temperature of about 5° C. followed by up to about 30 days at about 25° C. The storage temperature is preferably not lower than 0° C. The insulin at storage is preferably protected from exposure to light. The insulin premix formulation disclosed herein can be substantially unchanged by such storage (e.g., appearance, colour, pH, insulin concentration, and/or impurities). Therefore, the pharmaceutically acceptable insulin premix formulation as prepared by the method disclosed herein preferably has a shelf life of about 24 months at about 2-8° C. followed by about 30 days at about 25° C. when aseptically filled into a container. The container may be a glass container or a flexible container such as a plastic bottle or bag.

Another aspect of the present disclosure is a pharmaceutically acceptable insulin premix product comprising about 0.1-10.0 U/mL of insulin.

Non-limiting examples of the pharmaceutically acceptable insulin premix product comprises the pharmaceutically acceptable insulin premix formulation as disclosed and prepared herein above and a flexible container assembly, wherein the insulin premix formulation is aseptically filled into the flexible container assembly.

Non-limiting examples of the flexible container assembly may comprise a flexible container and optionally one or more port assemblies.

Non-limiting examples of the flexible container may have a volume of about 1.0 mL-1000.0 mL, preferably about 10.0-500 mL, more preferably about 50.0-300.0 mL and most preferably about 100.0 mL. The flexible container may be a flexible plastic container. The flexible container has an inner surface contacting the insulin premix formulation, wherein the inner surface is preferably made of a plastic material or a layer of plastic material. The plastic material is preferably selected from a group of polyethylene (PE), linear low density polyethylene (LLDPE), polyvinyl chloride (PVC), polypropylene (PP), copolymer, and modified polymer or copolymer. For example, the inner surface of the flexible container may be a PE. In one embodiment, the flexible container is a 100 ml GALAXY® single dose flexible container (PL 2501), which has an inner surface made of polyethylene (PE). The characteristics of non-limiting examples of suitable flexible containers are shown in FIG. 2.

Another aspect of the present disclosure is a pharmaceutically acceptable insulin premix product comprising a pharmaceutically acceptable insulin premix formulation in a flexible container assembly, wherein the pharmaceutically acceptable insulin premix formulation is disclosed and prepared herein above.

Non-limiting examples of the pharmaceutically acceptable insulin premix product may comprise about 0.1-10.0 U/mL, preferably about 0.5-5.0 U/mL, and more preferably about 0.5-2.0 U/mL, and most preferably about 1.0 U/mL of insulin in a flexible container assembly.

Non-limiting examples of the pharmaceutically acceptable insulin premix product preferably further comprise at least one tonicity adjuster.

Non-limiting examples of the pharmaceutically acceptable insulin premix product preferably further comprise at least one buffer.

Non-limiting examples of the pharmaceutically acceptable insulin premix product preferably have a pH value of about 6.5-7.2, preferably 6.6-7.0, and more preferably about 6.8.

Non-limiting examples of the pharmaceutically acceptable insulin premix product preferably have less than about 8.0%, more preferably less than about 5.0%, and most preferably less than about 4.0% of A-21 desamido insulin impurity by weight of the total insulin, when freshly prepared and through the shelf life of the product. The A-21 desamido insulin impurity is preferably less than about 4.0%, more preferably less than about 3.0%, most preferably less than about 2.5%, or even less than about 2.0% in the insulin premix product by weight of the total insulin when freshly prepared. The content of the A-21 desamido insulin impurity as disclosed herein is measured using a suitable reverse-phase HPLC method such as is provided in the USP monographs, adapted for use with concentration formulations.

Preferably, the pharmaceutically acceptable insulin premix product as disclosed and prepared herein is essentially free of any added zinc, any added preservative or any added surfactant, and may have improved stability and low concentration of impurities.

In some embodiments, the flexible container assembly may comprise a flexible container and preferably and optionally one or more port assemblies.

In some embodiments, the flexible container may have a volume of about 1.0-1000.0 ml, preferably about 10.0-500.0 ml, 50.0-300.0 ml, and more preferably about 100.0 ml. The flexible container may have an inner surface layer contacting the insulin premix solution, wherein the inner surface layer is made of a plastic material including PE, LLDPE, PVC, PP, copolymer and modified polymer or copolymer. For example, the flexible container is a 100 ml GALAXY® single dose flexible container (PL 2501) with PE inner surface. The characteristics of non-limiting examples of suitable flexible containers are shown in FIG. 2.

Preferably, the insulin in the pharmaceutically acceptable insulin premix product as disclosed and prepared herein does not adsorb or absorb to the flexible containers disclosed herein above. As is well known in the literature, insulin tends to bind to containers, including glassware containers and especially flexible plastic containers, such as polyethylene (PE) and polyvinyl chloride (PVC) containers. When insulin-containing solutions are placed in plastic containers, the fraction bound to the plastic has been reported to range from about 5% to about 80%. However, Applicant found that the insulin in the pharmaceutically acceptable insulin premix product as disclosed and prepared herein unexpectedly does not adsorb or absorb to any of the common flexible containers tested including PE and PVC containers. The characteristics of non-limiting examples of suitable flexible containers tested are shown in FIG. 2.

Another aspect of the present disclosure is a method of manufacturing a pharmaceutically acceptable insulin premix product. The method comprises 1) adding insulin to water and mixing until homogenous to form an aqueous solution with insulin in a concentration of about 0.1-10.0 U/mL; 2) adjusting pH of the aqueous solution to about 6.5-7.2; 3) sterilizing a flexible container assembly; and 4) aseptically filling the aqueous solution to a flexible container assembly.

Non-limiting examples of the method for manufacturing the pharmaceutically acceptable insulin premix product may comprise: 1) all the steps as disclosed above in the method for preparing the pharmaceutically acceptable insulin premix formulation as disclosed herein above; 2) sterilizing a flexible container assembly; and 3) aseptically filling the pharmaceutically acceptable insulin premix formulation as disclosed and prepared above into the sterilized flexible container assembly.

Non-limiting examples of the flexible container assembly may comprises a flexible container. In one embodiment, the flexible container assembly may further comprise at least one port assembly.

Non-limiting examples of the flexible container may be a flexible plastic container having an inner surface contacting the insulin solution, wherein the inner surface may be made of a plastic material, or a layer of plastic material. Preferred plastic materials for the inner surface contacting the insulin solution include polyethylene (PE), linear low density polyethylene (LLDPE), polyvinyl chloride (PVC), polypropylene (PP), copolymer, and modified polymer or copolymer. For example, the inner surface of the flexible container may be made of a flexible PE or LLDPE. The characteristics of non-limiting examples of the inner surface of common flexible containers are described in FIG. 2.

In one embodiment, the flexible container is a 100 ml GALAXY® single dose flexible container intended for intravenous drug infusion, such as GALAXY® PL 2501. The GALAXY® flexible container may be made of a single polymeric layer or multiple layers bonded together, or co-extruded. These film layers can comprise polymers such as, but not limited to, polyolefins, polyethers, and polyamides (nylon, for example). The inner surface of the GALAXY® flexible container is polyethylene (PE) or a layer of PE, which contacts the drug solution inside the bag.

In another embodiment, Applicant found that the insulin premix formulation as disclosed herein unexpectedly does not adsorb or absorb to the inner surface of the flexible containers regardless the types of flexible containers tested with or without the addition of an amino acid such as arginine, lysine, glycine; a sacrificial protein such as albumin; or a potassium salt such as KCl. Therefore, the insulin premix formulation as disclosed herein can significantly reduce insulin loss due to insulin adsorption or absorption to flexible containers and thus cut down medical errors in administration of the insulin to patients in need thereof in hospitals.

In another embodiment, the insulin loss of the pharmaceutically acceptable insulin formulation when stored in a flexible container is less than about 8.0%, preferably less than about 7.0%, more preferably less than about 6.0%, most preferably less than about 5.0%, or even less than about 4.0%, less than about 3.0% or less than about 2.0% by weight of the total insulin, wherein the insulin loss is due to a combination of insulin adsorption or absorption to the flexible container and insulin degradation, and the storage condition is one month, 3 months, 6 months, 12 months or 24 months at a refrigeration temperature of 2° C. to 8° C.

In another embodiment, the insulin loss of the pharmaceutically acceptable insulin formulation when stored in a flexible container is less than about 8.0%, preferably less than about 7.0%, more preferably less than about 6.0%, most preferably less than about 5.0%, or even less than about 4.0% by weight of the total insulin, wherein the insulin loss is due to a combination of insulin adsorption or absorption to the flexible container and insulin degradation, and the storage condition is 24 months at a refrigeration temperature of 2° C. to 8° C. followed by 1 month at room temperature of 23° C. to 27° C.

In yet another embodiment, the insulin loss of the pharmaceutically acceptable insulin formulation when stored in a flexible container is less than about 5.0%, preferably less than about 4.0%, more preferably less than about 3.0%, most preferably less than about 2.0%, or even less than about 1.0% by weight of the total insulin, wherein the insulin loss is due to a combination of insulin adsorption or absorption to the flexible container and insulin degradation, and the storage condition is one month, 3 months, 6 months, and 12 months at a refrigeration temperature of 2° C. to 8° C.

In yet another embodiment, the insulin in the pharmaceutically acceptable insulin formulation when stored in a flexible container essentially does not adsorb or absorb to the flexible container.

In yet another embodiment, the insulin loss of the pharmaceutically acceptable insulin formulation when stored in a flexible container is less than about 8.0%, preferably less than about 7.0%, more preferably less than about 6.0%, most preferably less than about 5.0%, or even less than about 4.0%, less than about 3.0%, less than about 2.0%, or less than about 1.0% by weight of the total insulin, wherein the insulin loss is due to insulin adsorption and/or absorption to the flexible container only, and the storage condition is 1 month, 3 months, 6 months, 12 months or 24 months at a refrigeration temperature of 2° C. to 8° C.

In another embodiment, the insulin loss of the pharmaceutically acceptable insulin formulation when stored in a flexible container is less than about 8.0%, preferably less than about 7.0%, more preferably less than about 6.0%, most preferably less than about 5.0%, or even less than about 4.0%, less than about 3.0%, or less than 2.0% by weight of the total insulin, wherein the insulin loss is due to insulin adsorption and/or absorption to the flexible container only and the storage condition is 24 months at a refrigeration temperature of 2° C. to 8° C. followed by 1 month at room temperature of 23° C. to 27° C.

In the disclosure herein, the percentage of insulin absorption and/or adsorption to the flexible container at different storage conditions and time periods is calculated by the following steps: 1) measuring the insulin concentration of the insulin premix formulation in the production tank after manufacturing but before filling into the flexible container (tank release insulin concentration); 2) measuring the insulin concentration in the flexible container at different storage conditions and time period; 3) measuring the concentration of A-21 desamido impurity and the concentration of the other insulin related substances in the flexible container at different storage conditions and time period; 4) subtracting the tank release insulin concentration by the concentrations of insulin, the A-21 impurity and the other insulin related substances in the flexible container at different storage conditions and time periods, to obtain the insulin concentration adsorbed and/or absorbed to the flexible container; and 5) dividing the insulin concentration adsorbed and/or absorbed to the flexible container at different storage conditions and time periods by the tank release insulin concentration.

Another aspect of the present disclosure is a method for glycemic control in an individual in an intensive care unit (ICU) with or without a history of diabetes mellitus before admitting into ICU. The method comprises administering an effective amount of a pharmaceutically acceptable insulin premix product to the individual, wherein the pharmaceutically acceptable insulin premix product is as disclosed and prepared above. The individual may be a mammal, and preferably a human including adults and children in need thereof.

Non-limiting examples of the method for administering the effective amount of the pharmaceutically acceptable insulin premix product may include parenteral administration.

Non-limiting examples of parenteral administration may preferably include intravenous administration, such as IV injection and IV infusion.

Preferably, the intravenous administration is IV infusion at room temperature such as about 25° C.

Another aspect of the present disclosure is a method of treating an individual having a metabolic disorder. The method comprises administering an effective amount of a pharmaceutically acceptable insulin premix product to the individual, wherein the pharmaceutically acceptable insulin premix product is as disclosed and prepared above. Non-limiting examples of metabolic disorders may preferably include diabetes mellitus, such as Type I and Type II diabetes.

Non-limiting examples of the administration of an effective amount of the pharmaceutically acceptable insulin premix product may include parenteral administration.

Non-limiting examples of parenteral administration preferably include intravenous administration, such as IV injection and IV infusion.

Preferably, the intravenous administration is IV infusion at room temperature such as about 25° C.

Preferably, the intravenous administration is under medical supervision for glycemic control in an individual at critical care units or for the treatment of an individual with metabolic disorders including diabetes mellitus, with monitoring of blood glucose and potassium concentration to avoid hypoglycaemia and hypokalemia.

Preferably, the intravenous (IV) administration of insulin premix formulation or product further comprises a step of flushing an IV administration set and/or a plastic tube with about 50.0-5000.0 ml of the pharmaceutically acceptable insulin premix formulation as disclosed and prepared herein above before the IV administration. The flushing step is to minimize the insulin loss due to the adsorption or absorption of insulin onto the IV administration set or the plastic tube.

EXAMPLES

The following non-limiting examples support the concept of using the pharmaceutically acceptable insulin premix formulation or product for glycemic control of an individual in an ICU, or for treatment of an individual having metabolic disorders including Type I and Type II diabetes mellitus.

Example 1

A study investigated the effect of buffers and storage conditions on the stability of different insulin premix formulations. The recombinant human insulin was manufactured by the Microbial Synthesis approach. The test articles and control articles were stored up to 25.5 months (110 weeks) at both about 5° C. and about 25° C., and for up to 24 weeks at about 40° C.

The samples were prepared according to the method shown in FIG. 3 in the following mixing procedures for 8.0 liters of each of the 1.0 U/mL insulin batches: (1) fill a glass beaker with approximately 6.4 liters (80% fill) of distilled water; (2) add 0.3 g of recombinant human Insulin and cloudiness appears; (3) add 0.1 N HCl gradually and adjust to pH of about 3.0, stir slowly until insulin completely dissolves; (4) add 0.1N NaOH drop wise to adjust to pH of about 7.4; (5) add the rest of the excipients and stir until dissolved; and (6) add distilled water to 8.0 L.

Sterile-fill the prepared samples into Autoclaved 50 ML ampoules at pH of about 7.4 (target). All the control articles for the study have 9.0 g of NaCl and 0.037 g of recombinant human insulin (27.1 U/mg) per liter, NaOH and HCl as needed to adjust pH and the following ingredients respectively.

1. Sample ID: Glass-PBS-2 mM, with formulation per liter shown below: $Na_2HPO_4$=0.23 g; $NaH_2PO_4.H_2O$=0.055 g. (2 mM phosphate buffer in final solution)
2. Sample ID: Glass-Arginine-2 mM, with formulation per liter shown below: L-Arginine=0.35 g. (2 mM arginine in final solution)
3. Sample ID: Glass-PBS-2 mM-(KCl-4 mM), with formulation per liter shown below: KCl=0.30 g; $Na_2HPO_4$=0.23 g (2 mM in final solution); $NaH_2PO_4.H_2O$=0.055 g. (2 mM phosphate buffer; and 4 mM KCl in final solution)

The test articles for the study are aseptically filled into 100 ml GALAXY® single use flexible containers (PL 2501) at a target pH 7.4 and include the following ingredients respectively:
1. Sample ID: PL2501-PBS-2 mM. The formulation per liter is the same as that of Sample ID Glass-PBS-2 mM.
2. Sample ID: PL2501-Arginine-2 mM. The formulation per liter is the same as that of Sample ID Glass-Arginine-2 mM.
3. Sample ID: PL2501-PBS-2 mM-(KCl-4 mM). The formulation per liter is the same as that of Sample ID Glass-PBS-2 mM-(KCl-4 mM).

The test results are recorded and shown in FIGS. 4-6 and FIGS. 7A-9B. FIGS. 7A and 7B are one figure split into two parts and FIG. 7B is a continued part of FIG. 7A, wherein FIGS. 7A and 7B show a comparison of the storage stability of the 1.0 U/mL of insulin with 2 mM of phosphate buffer in glass ampoules with that in PL2501 GALAXY® containers when stored at room temperatures (5±3° C.) over 110 weeks. Similarly FIGS. 8A and 8B are one figure split into two parts and FIG. 8B is a continued part of FIG. 8A, comparing the storage stability of the 1.0 U/mL of insulin with 2 mM of arginine in glass ampoules with that in PL2501 GALAXY® containers when stored at room temperatures (5±3° C.) over 110 weeks. FIGS. 9A and 9B are one figure split into two parts and FIG. 9B is a continued part of FIG. 9A, comparing the storage stability of the 1.0 U/mL of insulin with 2 mM of phosphate buffer and 4 mM of KCl in glass ampoules with that in PL2501 GALAXY® containers when stored at room temperatures (5±3° C.) over 110 weeks.

The test results include the insulin concentration, related substances, high molecular weight proteins (HMWP), instrumental particulate matter analysed by suitable standard methods known in the art for up to approximately 25.5 months (110 weeks) at storage temperatures of 53° C. and 25±2° C., and results for up to 24 weeks at 402° C.

Figure 6:
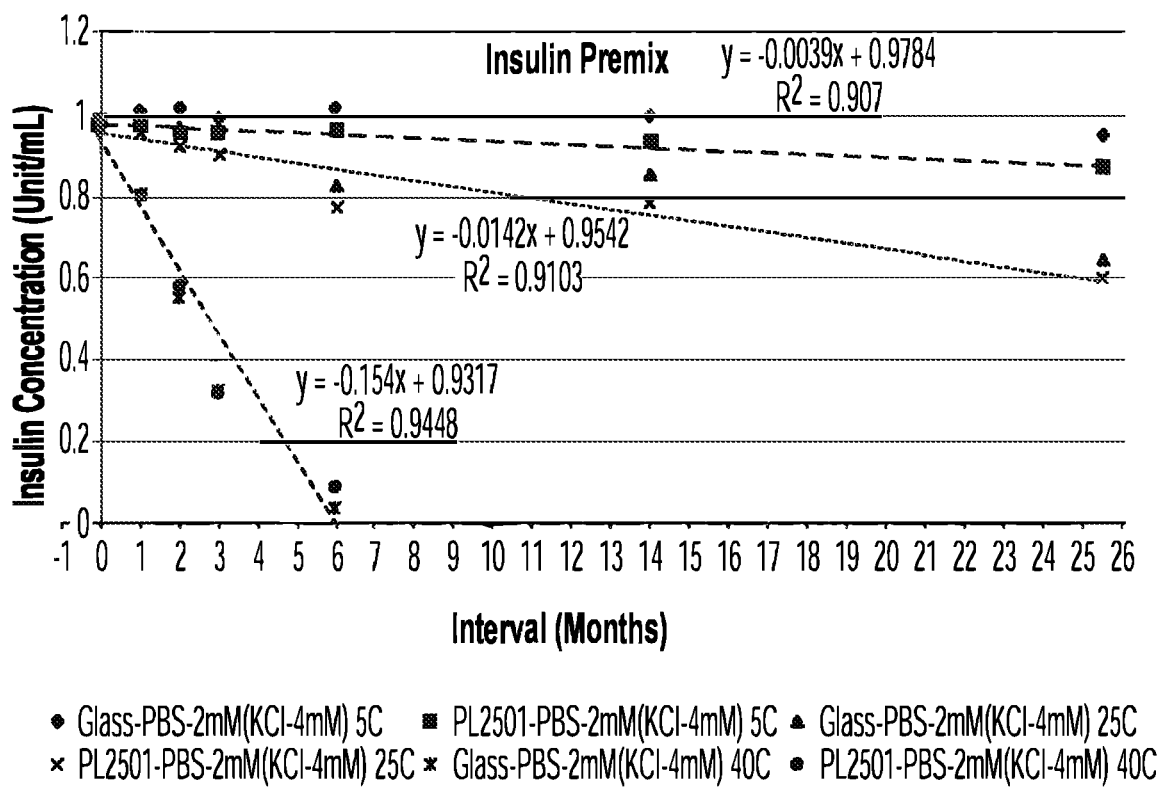

The experimental data demonstrate that all the insulin premix formulations with 1.0 Unit/mL tested in this study were stable for up to about 25.5 (110 weeks) when stored at refrigeration temperatures of 2° C. to 8° C. in PL 2501 GALAXY® containers, including the phosphate (PBS) formulation (see FIG. 4 and FIGS. 7A and 7B), the arginine formulation (FIG. 5 and FIGS. 8A and 8B), and the PBS and KCl formulation (see FIG. 6 and FIGS. 9A and 9B). The insulin concentration change was less than 10% for all the three formulations over the 110 weeks when stored at a refrigeration temperature of 2° C. to 8° C. in PL 2501 GALAXY® containers. The content of A-21 desamido insulin impurity was less than 4.0% as measured by reverse-phase HPLC for all the three formulations tested in this study over the 110 weeks stored at 5° C. It was noted that the pH of the arginine formulation drifted over the course of the study. The pH value change over the 110 weeks was more significant for the arginine formulation than that of the PBS formulation or the PBS and KCl formulation respectively. These experimental data suggest that that a buffering system would improve long term pH stability of the insulin premix formulation.

USP 34/NF 29 states that the limits applied to insulin human injection are potency of 95.0% to 105.0% in US insulin human units in each mL. The high molecular weight protein (HMWP) in USP limit is no more than 1.7% by weight of the total insulin and all three formulations are within the limit after about 25.5 months storage at 53° C. in a PL 2501 GALAXY® container.

Example 2

A study examined the effect of pH on the stability of insulin formulations at 1.0 Unit/mL concentration upon nominal storage (about 5° C.) and accelerated storage (about 25° C.). The insulin used in this study is a polypeptide hormone structurally identical to regular human insulin and was manufactured by recombinant DNA technology, utilizing *Pichia pastoris* (yeast) as the production organism.

The designed formulation used for this study is shown in the following: 1.0 U/mL of insulin; 0.9% of NaCl; 2.1 mM of Monobasic sodium phosphate; 2.9 mM of Dibasic sodium phosphate; and water to meet the concentration requirements of the listed ingredients. The sample preparation followed the method illustrated in FIG. 3 of the present specification, including the following mixing procedures: 1) filling a glass beaker to 90% of the final batch volume; 2) adding NaCl and mixing until dissolved to form a 0.9% salt solution by weight of the total formulation; 3) adding 2.1 mM of monobasic sodium phosphate and mixing until dissolved; 4) adding insulin in amount of 1.0 U/mL and mixing until dissolved; 5) adding dibasic sodium phosphate in amount of 2.9 mM and mixing until dissolved; and 6) adjusting pH as needed using NaOH and/or HCl.

The test articles consisted of units of the insulin injection product at four designed pH values of 6.5, 6.8, 7.0 and 7.2 (the actual measured pH for the samples was 6.44, 6.79, 6.97 and 7.22) respectively. The control articles were both samples removed directly from the mix tanks and stored in glass containers and samples of filtered solution stored in glass ampules. Test Articles (in GALAXY® bags) are denoted with a "T" in the formulation name while Control Articles (in glass ampules) are denoted with a "C" in the formulation name. The last two digits of the formulation name refer to the pH of the solution.

Test articles were stored long-term at the nominal product storage condition (about 5° C.), as well as, an elevated temperature condition (about 25° C.) to provide accelerated stability data. Replicate units of the test articles were removed from long-term storage and tested periodically according to the test time schedule. Control solutions were removed directly from the mix tank.

The test results are presented in FIGS. 10-13 (accelerated storage at about 25° C.) and FIGS. 14-17 (nominal storage at about 5° C.).

Zinc Content: During this study, the total content of zinc was measured for one of the samples. During the preparation process of the insulin premix formulation, no zinc was added to any of the formulations. The zinc content in the formulation (if any) came from the insulin raw materials. No zinc was added to the formulations apart from what existed in the insulin raw material. The content of the zinc in the insulin premix formulation was measured to be very low, about 0.13-0.16 µg/mL. In contrast, the zinc content of one of the commercially available concentrated insulin products is about 21 µg/mL per the package insert. Therefore, the insulin premix formulation has no more than 0.16 µg/mL of zinc which came from the insulin raw material, and was essentially free of any added zinc. The zinc content in the insulin premix formulation was much lower than that of the commercially available concentrated insulin products.

Visual Inspection: All test articles passed visual inspection through 6 months storage at 25° C. or through 24 months storage at 5° C. No visible particles, colour change or clarity change was observed for any of the tested articles.

pH value: There was no meaningful change in the pH value for any of the insulin formulations through 6 months of storage at room temperatures of about 25° C. (2° C.) or through 24 months of storage at refrigeration temperatures of about 5° C. (3° C.).

Osmolality: Osmolality values at all test intervals for all insulin formulations were between 293-298 mOsm/kg. There was no meaningful change in osmolality for any of the insulin formulations through 6 months storage at about 25° C. or through 24 months storage at about 5° C.

Instrumental Particulate Matter: All units tested were within the current USP instrumental particle limits for 100 mL Small Volume Injection (SVI) Solutions. The particulate matter (PM) larger than 10 µm is no more than 60 counts/mL, and the PM larger than 25 µm is no more than 6 counts/mL (for PM≥10 µm: no more than (NMT) 60 counts/mL and for PM≥25 µm: NMT 6 counts/mL).

High Molecular Weight Protein by Size-exclusion Chromatography (SEC): There were no dimers or aggregates above quantitation limit of 1.7% by weight of the total insulin, present in any of the insulin formulations through 6 months storage at about 25° C. or through 24 months storage at about 5° C.

Assay for Accelerated Storage (25° C.): Insulin assay values at all test intervals for all formulations were between 0.91-1.01 U/mL. Therefore, assay values remain within 90-110% of the target 1.0 U/mL concentration through 6 months of 25° C. storage. There was a general decrease in assay value in each formulation at this storage condition.

Assay for Nominal Storage (5° C.): Insulin assay values at all test intervals for all formulations were between 0.92-1.02 U/mL. Therefore, assay values remain within 90-110% of the target 1.0 U/mL concentration through 24 months of 5° C. storage. There was no discernible trend in assay value in any of the formulations at this storage condition.

Related Substances for Accelerated Storage (25° C.) Measured by Reverse-Phase HPLC: For all formulations, the concentrations of A-21 desamido insulin impurity increased over storage, however were less than 4.0% by weight of the total insulin after 2 months of storage at about 25° C., which were within the limit of A-21 impurity. The A-21 desamido insulin impurity increased to 7-9% at 6 months of storage at about 25° C. Other individual related substances were no more than 0.7% by weight of total insulin throughout this storage condition with no increasing trends observed.

Related Substances for Nominal Storage (5° C.) Measured by Reverse-Phase HPLC: For all formulations, the A-21 desamido-insulin impurity is less than 1.0% by weight of the total insulin after 24 months of storage of the formulation at the pH range from 6.5 to 7.2, which were within the 4.0% limit of A-21 impurity. Other individual related substances were no more than 0.6% (and total no more than 1%) by weight of the total insulin throughout this storage condition with no increasing trends observed.

Therefore, the experimental results demonstrated that the resulted insulin premix formulation with pH of about 6.5-7.2 is unexpectedly stable when freshly prepared and also during storage for up to 24 months at about 5° C. and surprisingly even at about 25° C. for 30 days or even up to 2 months. All of the test samples met the A-21 desamido insulin impurity requirement of less than 4.0% by weight of the total insulin when freshly prepared, for 24 months when stored at about 5° C., and for 2 months when stored at about 25° C. Consequently, the experimental results clearly demonstrated that the insulin premix formulations with pH of 6.5-7.2 prepared in this study were all stable for 24 months in storage at about 5° C. Further, the insulin premix formulations with pH of 6.5-7.2 prepared in this study were all stable for 30 days and even up to 2 months in storage at about 25° C.

Example 3

A study was conducted to investigate different means of insulin addition to the mix tank for the preparation of the insulin premix formulation. The following experimental factors were considered: 1) insulin solubility in 0.9 wt % of NaCl aqueous solution with different pH values; 2) foam production and dissipation as it relates to insulin concentration; 3) insulin addition as it relates to foam production; and 4) the feasibility of adding insulin as a solid or a slurry with undissolved insulin directly into the mixing tank without completely pre-dissolving the insulin.

The insulin used for this study is a recombinant human insulin manufactured using *Pichia pastoris* (yeast) as the production organism. Applicant found that potential homogeneity issues may exist in the batch tank when foaming occurs and when different mixing sequences were used. This study evaluated different insulin addition procedures that could be implemented to potentially alleviate dissolution concerns to reduce mixing time and improve the stability of the resulted products.

Insulin Solubility Limit Study:

7.7 g of insulin drug substance was added to an aqueous solution with 0.9 wt % of NaCl and 0.32 g/L of dibasic sodium phosphate (pH basic solution) for a total theoretically calculated concentration of 700 U/mL if the added insulin completely dissolves. After addition and mixing, there was a great amount of undissolved insulin and the actual insulin concentration was not tested. Similarly, 7.7 g of insulin drug substance was added for a total theoretically calculated concentration of 700 U/mL to the aqueous solution but with addition of HCl in amount of 0.01 N. After addition, the supernatant liquid was filtered and analyzed for insulin concentration to determine the solubility limit of insulin in the pH acidic solution. This set of experiments yielded an insulin slurry (basic pH conditions) and an insulin concentrate (acidic pH conditions) that were examined for use as potential insulin addition vehicles.

Insulin addition: Variability of insulin concentration values, throughout the dissolution procedure, appears to be greater in the batch in which insulin was added as a slurry (basic pH) with part of the insulin undissolved. The batch with 0.01 N HCl (acidic pH) in which insulin was added as a slurry took less time to reach visible dissolution. Therefore, while both means of addition of insulin to the mix tank are feasible, the acidic pH route would result in faster dissolution of insulin and thus reduced mixing time.

The experimental results demonstrated that the solubility limit of insulin in 0.01 N hydrochloric acid is about 637 U/mL, which would inform the maximum concentration of an insulin concentrate prepared under acidic conditions. The solubility of insulin in water (neutral pH condition) or in dibasic sodium phosphate (basic pH condition) was not measured, but is visually much lower than that in 0.01 N HCl solution. From the experimental results, it is clear that insulin dissolves much faster in the acidic solution; and insulin addition to a batch as either a concentrate below the solubility limit or as a slurry with undissolved insulin is feasible. Therefore, a step of adjusting the pH of the aqueous solution to be about 2.0-5.0 was selected before the addition of insulin in the powder form for the method of making the final insulin premix product in order to dissolve the insulin in the solution quickly and thus to reduce mixing time and to achieve consistency of the product.

Foam Production and Dissipation:

The test solution was 3000 mL of the insulin formulation test solution stored at about 5° C. The test solution was sampled six times, from different locations within the container, for insulin concentration testing while there was no foam present. This same test solution was then mixed at 600 rpm for 5 minutes with an overhead mixer to produce foam and then sampled for insulin concentration testing as above. The same test solution was again mixed at 600 rpm for 5 more minutes to produce more foam and then sampled for insulin concentration testing as above.

Three 200 mL portions of the test solution and each portion was analyzed for insulin concentration and related substances under the following conditions: 1) no foam; 2) immediately after foam was produced (600 rpm for 5 minutes); and 3) after produced foam (600 rpm for 5 min.) was completely dissipated.

Test results are shown in FIGS. 18-19. When foam was produced in the insulin formulation, part of the insulin was trapped into the foam. The difference in insulin concentration, from the no foam condition to foam condition, was only about −1% (FIGS. 18-19). When more foam was produced, the difference was about 4%. When foam was produced in the insulin formulation, although about 2% less insulin was measured (FIG. 19), the insulin chromatographic profile (percentage of desamidos) did not appreciably change. When foam subsides, the insulin concentration appears to return to the initial (no foam) value.

The experimental results demonstrated that the measured insulin concentration decreases as a result of foam production in an insulin formulation, without having an effect on the chromatographic profile of the formulation. The measured insulin concentration returns to initial value after foam production has completely subsided. However, waiting for the foam to subside would take a longer time for the manufacturing process and is therefore less desirable.

As noted above, insulin addition to a batch as a solid, a slurry with undissolved insulin or a concentrate with completely dissolved insulin are all feasible. It is desirable to first adjust the pH of the aqueous solution to about 2.0-5.0 before the addition of insulin to ensure faster insulin dissolution. The mixing sequence is important for the quick dissolution of insulin into the aqueous solution and foam reduction. Adjusting the pH of the aqueous solution to be about 2.0-5.0 before the addition of insulin minimizes foam formation during the process, reduces the total mixing time and further ensures the consistency of the insulin concentration of the final product. Furthermore, it is advantageous to use low speed mixing to minimize foam formation during the mixing process.

Example 4

A study was conducted to investigate the insulin absorption/adsorption onto different types of flexible containers suitable for IV infusion. This study further determined the effect of pH and addition of different excipients (Arginine, glycine, lysine and human albumin serum) on the insulin absorption/adsorption to different types of flexible containers.

The insulin formulation (1.0 Unit/mL) was filled into various types of flexible containers and glass ampoules to assess the change with respect to visual inspection, pH value, insulin concentration, and impurities. This study further evaluated the effects of different excipients on the insulin adsorption or absorption to flexible containers at different pH values.

The control articles in this study were the premix insulin formulation filled into glass ampoules. Approximately 5-10 ampoules of each formulation were produced. The test articles were the insulin premix formulations filled into different types of 100 ml flexible bags. The description of different bag types tested is shown in FIG. 2.

The formulation samples for the insulin premix injection at 1.0 U/mL with or without 1.0 mg/mL Human Albumin spiking were prepared according to the mixing procedures illustrated in FIG. 3. The insulin concentration in different plastic containers was measured within one week after the insulin premix formulation was filled into the flexible container. The experimental results for all testing performed are summarized in FIGS. 20-22.

pH Value: No change in pH from tank sample was observed in any of the flexible containers with the premix insulin formulation, 1.0 U/mL (with or without Albumin spiking).

Assay and Related Substances: Insulin assay results are shown in FIGS. 20-22. The change in percentage of total insulin as compared to the tank sample was relatively small and was comparable in all of the flexible containers with all samples. Addition of Albumin to the insulin premix formulation did not result in a significant difference in insulin concentration compared to formulations without albumin. The insulin loss for all containers including PVC containers are similar and are also relatively small and within 5% of the insulin concentration from the control articles (Samples from the tank). The experimental results in this study clearly demonstrated that the insulin in the insulin premix formulations or products as prepared in this study unexpectedly does not adsorb or absorb to any of the flexible containers tested, regardless of Albumin addition.

As is well known in the literature, insulin tends to bind to containers, including glassware containers and especially flexible plastic containers, such as polyethylene (PE) and polyvinyl chloride (PVC) containers. When insulin-containing solutions are placed in plastic containers, the fraction bound to the plastic has been reported to range from about 5% to about 80%.

However, Applicant surprisingly found that the insulin in either of the pharmaceutically acceptable insulin premix formulation or product as disclosed and prepared herein unexpectedly does not adsorb or absorb to common flexible containers suitable for IV infusion, including PE and PVC containers. The characteristics of the flexible containers tested are shown in FIG. 2. The plastic materials of the inner surface contacting the insulin solution include, PE LLDPE, PVC, PP, copolymer, and modified polymer or copolymer. The experimental results demonstrated that the insulin in either of the pharmaceutically acceptable insulin premix formulation or product as disclosed and prepared herein unexpectedly does not adsorb or absorb to the flexible containers regardless of the types of the plastic materials of the inner insulin contacting surface tested.

Figure 23:
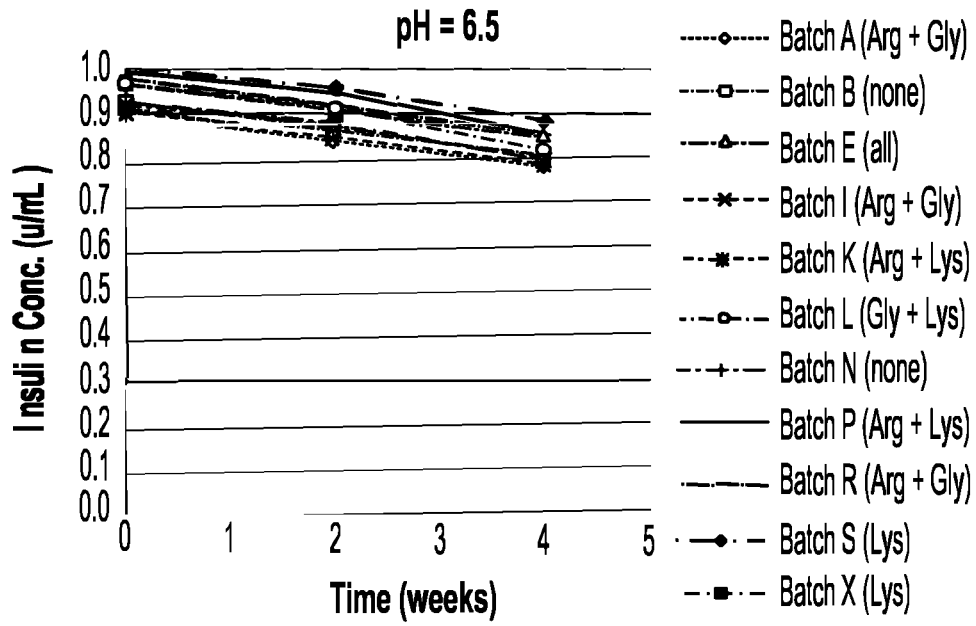
Figure 24:
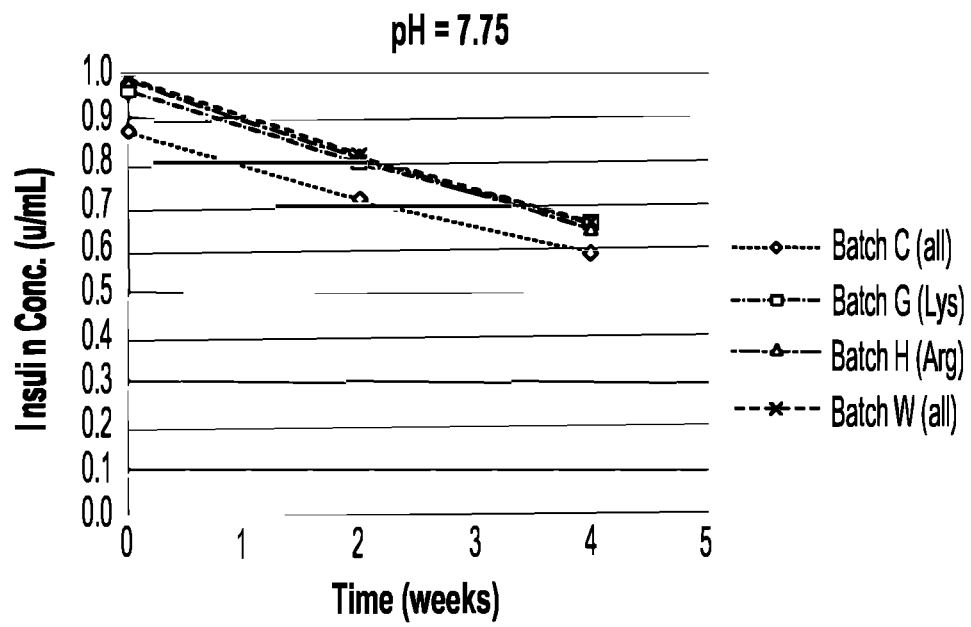
Figure 25:
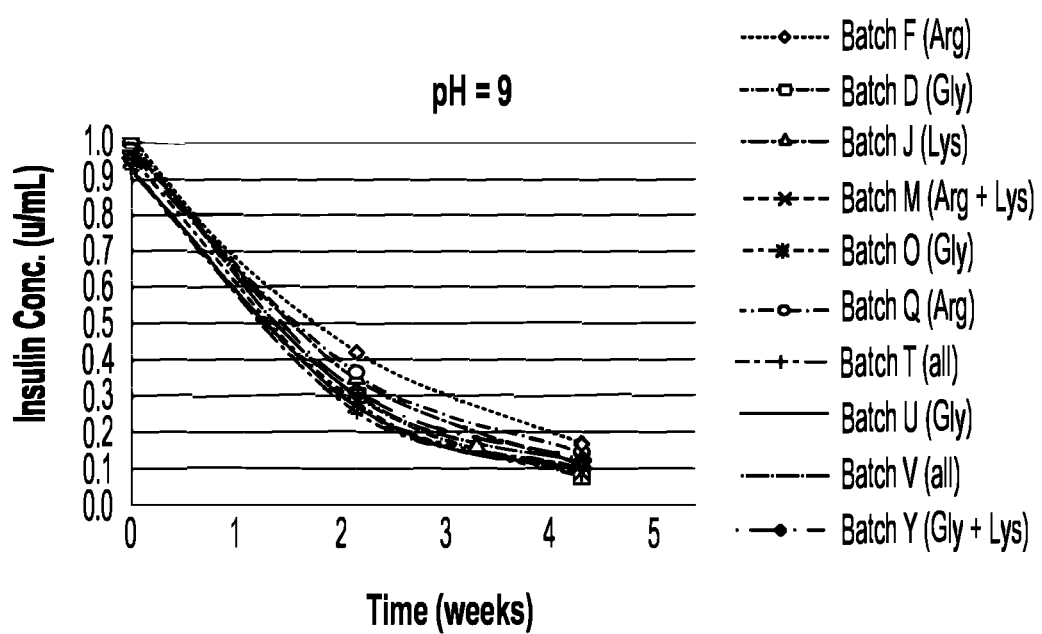

The effects of pH and the addition of different excipients on insulin adsorption onto and stability in a flexible container: Further in this study, the pH and the addition of different excipients on insulin adsorption/absorption onto and stability in a flexible container were also investigated over 4 weeks of storage in the flexible container at about 40° C. The experimental results are shown in FIGS. 23-25. From the experimental data in FIGS. 23-25, it is clear that, the pH of the insulin premix formulation significantly affects the insulin loss due to adsorption/absorption to the flexible containers or degradation over the storage. The higher the pH, the higher amount of the insulin loss. Further, the addition of different excipients such as arginine, lysine and glycine did not have meaningful effects on the insulin adsorption/absorption to the flexible containers or the stability of insulin in the flexible containers over the storage at 40° C. for 4 weeks.

Example 5

A study was conducted to investigate the effect of the addition and mixing sequence of ingredients on solubility of insulin and stability of the insulin in the insulin premix formulations. The manufacturing method detailed in FIG. 3 was used for this study.

The formulation contains about 1.0 U/mL of insulin based on the total formulation, 0.9% sodium chloride by weight of the total formulation, and a combination of monobasic sodium phosphate and dibasic sodium phosphate in a total amount of 5.0 mM based on the total formulation, sodium hydroxide (NaOH) and hydrogen chloride (HCl) as needed to adjust the pH value of the formulation, and water to meet the concentration requirements of the listed ingredients. The molar ratios of monobasic sodium phosphate and dibasic sodium phosphate tested are 2.1:2.9; 2.2:2.8; 2.3:2.7; 2.4:2.6; 2.5:2.5 and 2.6:2.4 respectively.

The test articles for this study were solutions of insulin in normal saline with various molar ratios of monobasic sodium phosphate to dibasic sodium phosphate added. These test articles were prepared in triplicate using several addition orders as follows:

Test Article #1: 18 solutions were prepared (6 phosphate ratios in triplicate). Two additional phosphate ratios beyond those specified in the protocol were prepared and tested.
1. Appropriate vessels were filled with 450 mL water each (about 90% of final volume) for each of 18 preparations.
2. NaCl was added and mixed to dissolve (target amount for a 500 mL solution=4.5 g for each of 18 preparations). pH was recorded. The pH for these solutions ranged from 5.54-5.94.
3. Monobasic sodium phosphate (monohydrate) and dibasic sodium phosphate (anhydrous) were added in the molar ratios of 2.1:2.9; 2.2:2.8; 2.3:2.7; 2.4:2.6; 2.5:2.5; and 2.6:2.4. The solutions were mixed to dissolve and the pH was recorded. The pH values for all the solutions were ranged from about 6.61 to about 6.78, as shown in FIG. 26.
4. Insulin was added (target amount for a 500 mL solution=18.74 mg for each preparation) and the solutions were mixed.
Visual inspection was used to determine if the insulin dissolved. After 30 minutes, the insulin had not dissolved, and solution preparations were discontinued.

Test Article #2: 3 solutions were prepared.
1. Appropriate vessels were filled with 450 mL water (about 90% of final volume (target final volume=500 mL for each of 3 preparations)).
2. NaCl was added and mixed to dissolve (target amount for a 500 mL solution=4.5 g for each of 3 preparations). The pH for these solutions was 5.16-5.75.
3. Insulin was added (target amount for a 500 mL solution=18.74 mg) and mixed to dissolve.
Visual inspection was used to determine if the insulin dissolved. After 30 minutes, the insulin had not dissolved, and solution preparations were discontinued.

Test Article #3: 3 solutions were prepared.

1. Appropriate vessels were filled with 450 mL water (about 90% of final volume (target final volume=500 mL for each of 3 preparations)).
2. NaCl was added and the solutions were mixed to dissolve (target amount for a 500 mL solution=4.5 g for each of 3 preparations).
3. Monobasic sodium phosphate (monohydrate) was added to each solution (target amount for a 500 mL solution=172.5 mg for each of 3 preparations), and mixed to dissolve. The pH was measured and recorded to be about 4.76-4.78.
4. Insulin was added (target amount for a 500 mL solution=18.74 mg) and mixed to dissolve. Visual inspection was used to determine if the insulin dissolved. After 25 minutes, the insulin had dissolved.
5. Dibasic sodium phosphate (anhydrous) was added to the solutions (target amount for a 500 mL solution=177.5 mg for each of 3 preparations). They were mixed to dissolve, and the pH was measured. The pH of these solutions was measured to be about 6.62-6.65.
6. The solutions were added water to 100% volume (500 mL), and the pH was measured. The final pH was 6.65-6.66.

Test Article #4: 3 solutions were prepared.
1. Appropriate vessels were filled with 450 mL water (about 90% of final volume (target final volume=500 mL for each of 3 preparations)).
2. NaCl was added and mixed to dissolve (target amount for a 500 mL solution=4.5 g for each of 3 preparations). The pH was 6.16-6.28.
3. Dibasic sodium phosphate (anhydrous) was added to each solution (target amount for a 500 mL solution=177.5 mg for each of 3 preparations) and mixed to dissolve. The pH was 8.31-8.51.
4. Insulin was added (target amount for a 500 mL solution=18.74 mg) and mixed to dissolve. Visual inspection was used to determine if the insulin dissolved. After 10 minutes, the insulin had dissolved.
5. Monobasic sodium phosphate, monohydrate was added to each solution (target amount for a 500 mL solution=172.5 mg for each of 3 preparations) and mixed to dissolve. The pH was 6.61-6.63.
6. The solutions were added with water to 100% volume (500 mL), and the pH was measured. The final pH was 6.64-6.65.

Data Analysis: Insulin dissolution in this study can be summarized as follows: In Test Article #1, sodium chloride and both sodium phosphates (monobasic and dibasic) were combined before insulin was added. Insulin failed to dissolve after 30 minutes of stirring at room temperature at pH ~6.61-6.78. In Test Article #2, insulin was added to a solution of sodium chloride in water. Insulin failed to dissolve after 30 minutes of stirring at room temperature at pH ~5.07-5.61. In Test Articles #3, sodium chloride and monobasic sodium phosphate were combined, and then insulin was added to the solution. In Test Article #4, sodium chloride and dibasic sodium phosphate were combined, and then insulin was added. In both cases, the insulin dissolved within 30 minutes of stirring at room temperature at pH ~4.76-4.78 (for Test Article #3, monobasic sodium phosphate) or pH ~8.31-8.51 (for Test Article #4, dibasic sodium phosphate).

The experimental data demonstrated that insulin could be dissolved in aqueous solution having a pH less than about 5.0 or at a pH of about 8.31-8.51 within 30 minutes at room temperature (about 25° C.). However, insulin is not stable in pH basic solutions, and so using acidic solutions to dissolve the insulin is the preferred route. The addition sequence of the ingredients impacts the mixing time and the necessity of pH adjustment (to be within the pH range of about 6.5-7.2) using NaOH or HCl. For the test article #3, the pH of the final product is about 6.65-6.66 which is within the pH range of 6.5-7.2 that provides for a stable formulation, and thus the need for pH adjustment using NaOH or HCl is minimized.

Based on the data collected in this study, a preferred mixing order for an exemplary formulation is as follows: 1) fill tank to 90% of final batch volume with water; 2) add sodium chloride and mix to dissolve; 3) add monobasic sodium phosphate and mix to dissolve; 4) add insulin and mix to dissolve; 5) add dibasic sodium phosphate and mix to dissolve; 6) test and adjust pH to about 6.5-7.2 if needed using NaOH/HCl; and 7) add water to 100% of final batch volume and mix until homogenous.

A preferred molar ratio of monobasic sodium phosphate (monohydrate) to dibasic sodium phosphate (anhydrous) to use in order to achieve a pH near the center of the preferred pH range of 6.5-7.2, or 6.8, with minimal adjustment is 2.1:2.9. This ratio equates to 0.290:0.412 (mg/mL) monobasic sodium phosphate:dibasic sodium phosphate. It is preferred to add the monobasic sodium phosphate before the addition of insulin (as opposed to the dibasic sodium phosphate) so that the pH of the insulin solution stays at or below the preferred pH range. Insulin solutions are not stable in pH basic media, and so using acidic solutions to dissolve the insulin is the preferred route.

Further study was performed to evaluate the effects of using HCl to adjust the pH value of the aqueous solution before the addition of insulin.

The test articles for this study were solutions of insulin in normal saline at pH ~3 (3.0±0.3) with various ratios of monobasic sodium phosphate monohydrate and dibasic sodium phosphate anhydrous added. The control articles for this study were the insulin solutions in normal saline without any phosphates added.

A stock solution at pH ~3 (3.0±0.3) of insulin in normal saline was prepared and aliquoted into smaller portions. Monobasic sodium phosphate and dibasic sodium phosphate were added to the aliquots in various ratios to obtain the Test Articles. The mixing process is described below: 1) An appropriate vessel was filled with water to about 90% of final volume (450 mL was used as the 90% for each of 3 preparations); 2) NaCl was added and mixed to dissolve (target amount for a 500 mL solution=4.5 g for each of 3 preparations); 3) pH was adjusted to ~3 (3.0±0.3) using 0.1N HCl; 4) Insulin was added and mixed until dissolved (target amount for a 500 mL solution=18.8 mg for each of 3 preparations); 5) add water to 100% volume and mix until homogenous; and 6) Solution was aliquoted into 5 portions (target 100 mL each for each of 3 preparations; there were 15 aliquots total). Phosphates were added according to FIG. 27.

The pH was measured for the solutions prepared as test and control articles. The results of the pH measurements are given in FIG. 27. The difference from the target pH value of 6.8 was calculated for each of the Test and Control Article averages (n=3). The differences are given in FIG. 27.

Based on the results of this study, a molar ratio of 1.175:3.825 mmol/L monobasic sodium phosphate: dibasic sodium phosphate is predicted to be the appropriate ratio for use in future insulin studies where a target pH of 6.8 is desired. In terms of mg/mL phosphates, this ratio is 0.162 mg monobasic sodium phosphate and 0.543 mg dibasic sodium phosphate per mL of solution. This ratio can be used in cases where the insulin is added as an acidic concentrate.

Example 6

In this Example, data from two separate studies is combined to demonstrate how one of the preferred formulations was discovered. The first study is a Design of Experiments (DOE) study. The DOE methodology is employed to examine the effects of multiple variables at the same time such that a "knowledge space" can be built around the formulation(s) being studied. Once the "knowledge space" has been determined, predictive modeling can be used to suggest an optimized formulation the will be carried on to further study. For the DOE study, the pH was varied from 6.5-9, and the amino acid stabilizers were varied from 0-10 mM. The phosphate buffer strength was held constant at 5 mM and the NaCl concentration was held constant at 0.9%. The amino acid stabilizers used were glycine, lysine, and arginine. Twenty-five different formulations were prepared and their degradation behavior was studied at various temperatures in order to build predictive models of formulation behavior.

Figure 30:
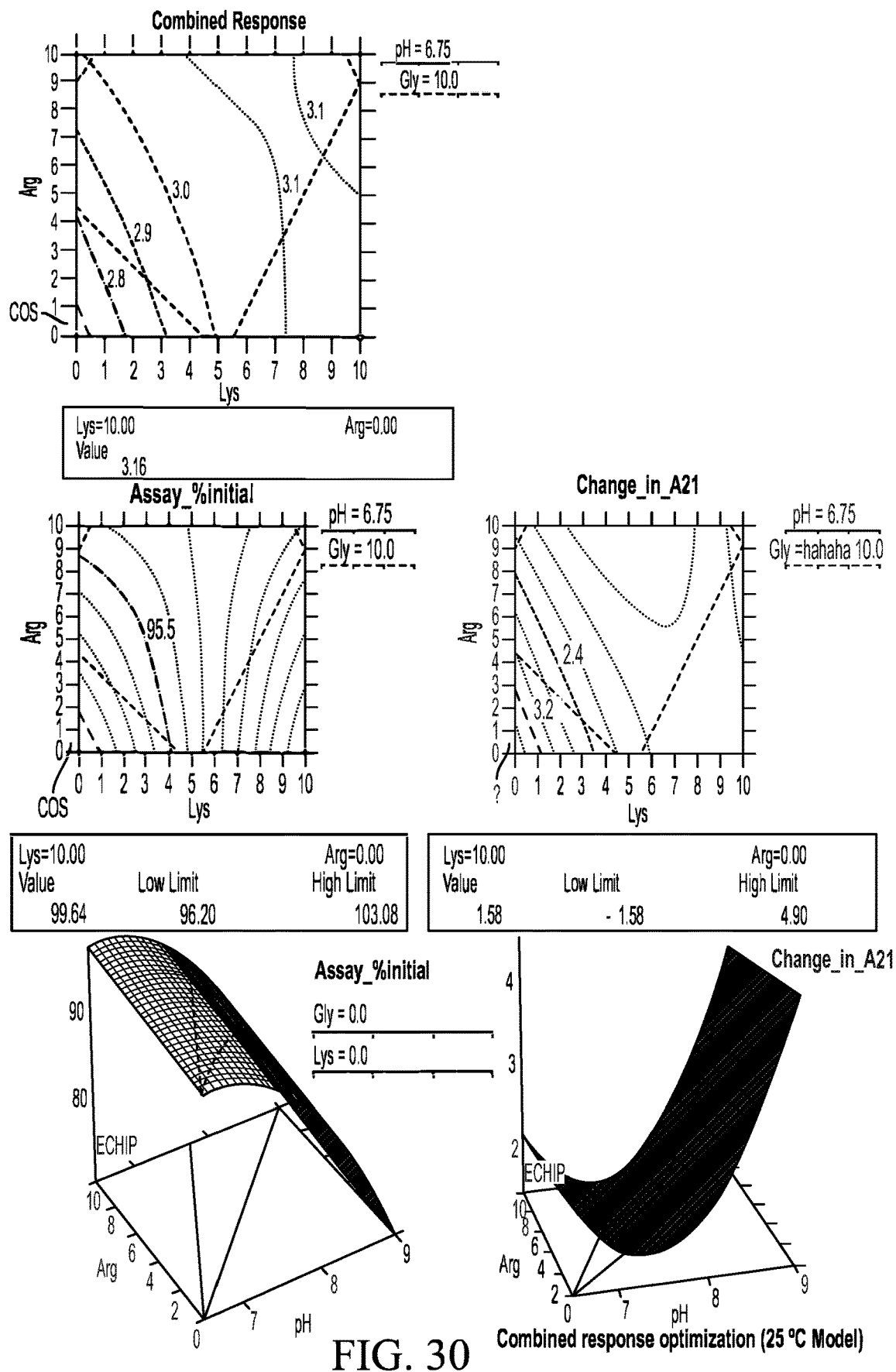

The model generated from the 25° C. data is described further in this example. The data was analyzed to optimize both the assay (insulin concentration) drop over time and the formation of the A-21 desamido impurity. Once the model was built, a grid search was performed to locate the parameters predicted to yield the most stable formulation with respect to each of these parameters. The results of the grid search for Assay loss are shown in FIG. 28. The results of the grid search for minimization of A-21 desamido formation are shown in FIG. 29. A combined response surface was also generated for this Model as shown in FIG. 30 and FIG. 31. Overall, this study suggests that an optimal target pH will be around 6.5-6.9, with pH 6.8 preferred to reduce formation of the A-21 desamido impurity. The content of the A-21 insulin impurity as disclosed herein was measured by reverse-phase HPLC.

The second study in this Example is a traditional long-term formulation feasibility study. Several different formulations were tested in this study to help determine an optimum pH, phosphate level, and arginine level in the formulation. The pH ranged from 7.0-7.8, the arginine level ranged from 0-5 mM, and the phosphate level was either 2 or 5 mM. This study was conducted in parallel with the DOE study described above and hence the outcome of the ideal pH range was not yet known. Data on these formulations was collected for up to 23 months of long term storage in both GALAXY® and glass containers at about 5° C.; and up to 6 months of storage in both GALAXY® and glass containers at about 25° C. The experimental results for formulations with about 5 mM phosphate and about 2 mM arginine having pH of 7.0, 7.4 and 7.8 are shown in FIGS. 32-34 for storage up to 23 months at about 5° C., and in FIGS. 35-37 for storage up to 6 months at about 25° C. to exemplify the pH effects on insulin premix properties over the storage.

The experimental data collected through the 23 months intervals at about 5° C. showed that the insulin formulations were very stable over the storage time of 23 months when stored at about 5° C. in both the GALAXY® containers and the glass containers. The data further demonstrated that the formulation having pH of about 7.0 showed better long-term stability than that of the formulations having pH of 7.4 and 7.8 respectively. For example, the A-21 desamido insulin impurity and the total related substances for the formulation having pH of 7.0 were lower than those of the formulations having pH of 7.4 and 7.8 respectively.

The experimental data collected through the 6 months intervals at about 25° C. showed those samples had degradation after storage at about 25° C. for more than 3 months. Experimental results in FIGS. 35-37 clearly demonstrated that the formulation having pH of 7.0 showed better stability over the storage time of 6 months at about 25° C. For example, the formulation having pH of 7.0 had much less HMWP, less protein fragmentation, and also less total related substances than those of the formulations having pH of 7.4 and 7.8 respectively.

There were no significant differences in long-term stability between the samples stored in the GALAXY® containers and the glass containers at either temperatures of about 5° C. or about 25° C.

Therefore, the experimental data suggests that the insulin formulations are as compatible with the GALAXY® containers as they are with glass containers with regard to lack of protein adsorption, aggregation, and degradation. Protein fragmentation was only seen at the 25° C. storage condition. All formulations in GALAXY® containers maintained more than 95% of their initial insulin concentrations (as measured by UHPLC) for 23 months when stored at about 5° C. The A-21 desamido percentage was less than 3.0% by weight of the total insulin as measured by reverse-phase HPLC in all the formulations tested for up to 23 months when stored at about 5° C. Insulin potency was maintained at 1.0 U/mL throughout this 23 month study for the refrigerated samples stored at about 5° C.

Furthermore, the experimental data in FIGS. 38-39 demonstrated that the arginine level does not have a meaningful impact on the stability of insulin premix formulations in the ranges used in this study. Based on the results of this study, the arginine excipient does not significantly enhance formulation stability. Therefore, arginine is deemed not necessary for the stabilization of these formulations.

Example 7

A study was performed to investigate the long term stability of the insulin premix formulation over storage for 24 months at refrigeration temperatures of 2° C. to 8° C. followed by 30 days at room temperatures of 23° C. to 27° C.

The formulation contains about 1.0 U/mL of insulin based on the total formulation, about 0.9 wt % sodium chloride of the total formulation, a combination of monobasic sodium phosphate and dibasic sodium phosphate at a molar ratio of 2.1:2.9 and in a total amount of about 5.0 mM, and sodium hydroxide and/or hydrogen chloride as needed to adjust the pH value of the formulation to about 6.8. Total three different batches of production samples were manufactured and tested at different storage conditions and intervals.

The preparation method, as illustrated in FIG. 3 of the present specification, included the following mixing procedures: 1) filling a tank to 90% of the final batch volume; 2) adding NaCl and mixing until dissolved to form a 0.9% salt solution by weight of the total formulation; 3) adding 2.1 mM of monobasic sodium phosphate and mixing until dissolved; 4) adding insulin in amount of 1.0 U/mL and mixing until dissolved; 5) adding dibasic sodium phosphate in amount of 2.9 mM and mixing until dissolved; 6) adjusting pH as needed using NaOH and/or HCl to form the insulin premix formulations; and 7) adding water to the final batch volume and mixing until homogeneous to form the insulin premix formulation.

The total test period included 24 months stored at refrigeration temperatures of 2° C. to 8° C. followed by 30 days stored at room temperatures of 23° C. to 27° C. At different intervals during the storage, samples were taken out from the storage for testing. The experimental results for the original samples (control), the samples after 24 months of storage at 2° C. to 8° C., and the samples after 24 months of storage at 2° C. to 8° C. followed by 30 days at room temperatures of 23° C. to 27° C. are shown in FIG. 40.

In this study, insulin, A-21 desamido insulin impurity and insulin related compounds were separated and measured by reverse-phase high performance liquid chromatography (HPLC) or UHPLC using a C18 column. The detection was performed using UV at 214 nm wavelength. The analytical method was adapted for low concentration formulations from that provided in the USP monograph for insulin, which contains detailed instructions for performing this analysis. The insulin related compound quantification was performed using percent response (area under the curve of the peak) within the sample injection. The HPLC peak areas are determined by standard integration programs available in HPLC software (e.g. Empower). The peak areas thus determined are compared to those of a standard solution in order to perform quantitation.

Figure 41:
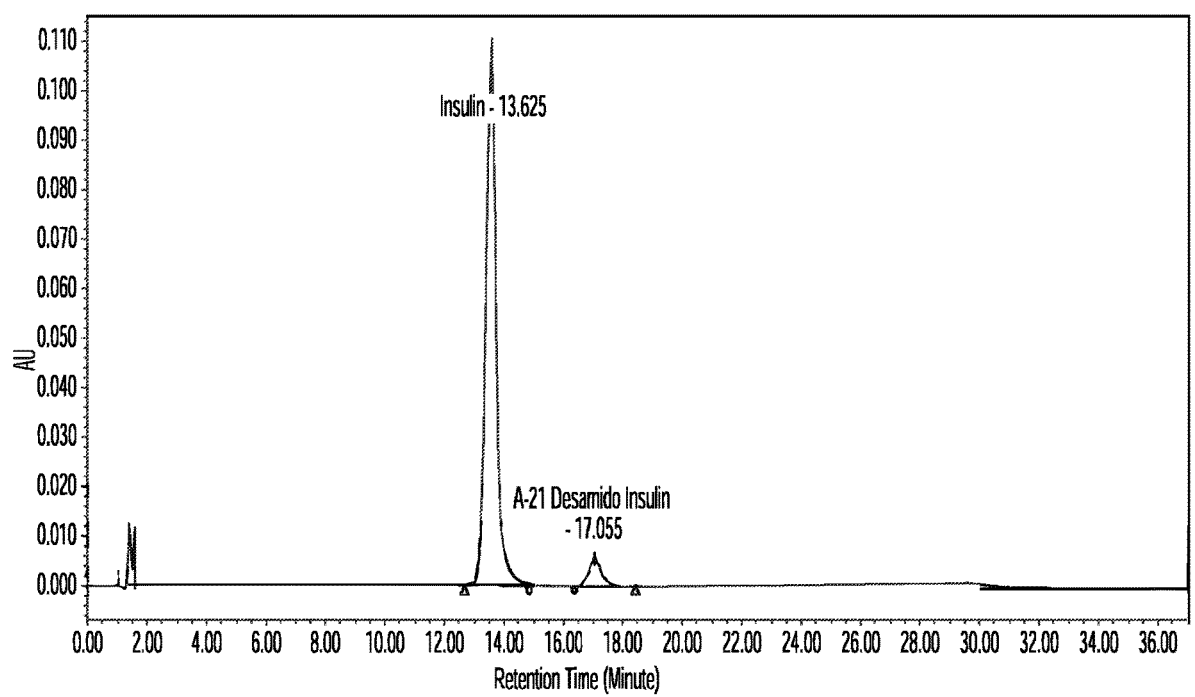
FIG. 41 shows the test results of the experimental study in Example 7 disclosed herein.

One example of the HPLC chromatograms is provided in FIG. 41 to illustrate the separation of the insulin and the A-21 desamido insulin peaks, and the measurement of the A-21 desamido insulin impurity content. This example is provided for illustrative purposes only. It will be understood to those skilled in the art that peak retention times may shift when different HPLC systems, columns, mobile phase preparations, etc. are used.

The contents of A-21 insulin impurity as disclosed and prepared in this study and in the present specification were all based on the peak area under the curve as measured by the reverse-phase HPLC method using UV at 214 nm wavelength for detection. The identity of the A-21 desamido insulin peak is confirmed based on matching its retention time with that of the A-21 desamido insulin peak in the System Suitability Solution as provided in the USP insulin monograph.

The concentrations of insulin dimer, hexamer or any other high molecular weight protein (HMWP) were also measured using a suitable size exclusion chromatography (SEC) method such as the one provided in the USP insulin monographs; adjusted for use with low concentration insulin preparations in this study. The total concentrations of the insulin dimer, hexamer or any other high molecular weight protein (HMWP) were no more than 1.1% by weight of the total insulin for the samples.

The experimental results demonstrated that the insulin premix formulations were very stable over the entire storage period for all the four different batch samples. For example, as shown in FIG. 40, the pH values for all the four batch samples were maintained constant at around 6.8-6.9 through the entire storage period, which is within the pH limit of 6.5-7.2. The changes of the insulin concentrations for all the four batch samples were no more than 3.0% through the end of the storage period, which is within the limit of 10% of the original insulin concentration when freshly prepared. The A-21 desamido insulin impurity was less than 1.5% by weight of the total insulin (as measured by reverse-phase HPLC) for all the tested samples over the entire storage period. Furthermore, the total concentrations of the insulin dimer, hexamer or any other high molecular weight protein (HMWP) were no more than 1.1% by weight of the total insulin as measured by SEC for all the four different batch samples over the entire storage period.

Furthermore, the test results in FIG. 40 also demonstrated that the insulin in the product essentially does not absorb or adsorb to the flexible container, the GALAXY® PL 2501 container. The total insulin loss (except for Lot No. 2) (due to a combination of insulin adsorption and/or absorption to the flexible container, and insulin degradation) was less than 2.0% by weight of the total insulin when the premix product was freshly prepared; less than 2% by weight of the total insulin after the premix product was stored for 24 months in the refrigeration temperature of 2° C. to 8° C.; and less than 5% by weight of the total insulin after the premix product was stored for 24 months at the refrigeration temperature of 2° C. to 8° C. followed by 1 month at room temperature of 23° C. to 27° C. The total insulin loss for Lot No. 2 was less than 4.0% by weight of the total insulin when the premix product was freshly prepared; less than 6.0% by weight of the total insulin after the premix product was stored for 24 months in the refrigeration temperature of 2° C. to 8° C.; and less than 7.0% by weight of the total insulin after the premix product was stored for 24 months at the refrigeration temperature of 2° C. to 8° C. followed by 1 month at room temperature of 23° C. to 27° C. The total insulin loss was due to a combination of insulin absorption and/or adsorption to the flexible container, the insulin degradation.

The experimental results in FIG. 40 further demonstrated that the adsorption and/or absorption of insulin of the insulin premix product to the flexible container (except for the Lot No. 2) was less than 2.0% when the premix product is freshly prepared; less than 2.0% after the premix product was stored for 24 months at the refrigeration temperature of 2° C. to 8° C.; and less than 3.0% after the premix product was stored for 24 months at the refrigeration temperature of 2° C. to 8° C. followed by 1 month at room temperature of 23° C. to 27° C. The adsorption and/or absorption of insulin of the insulin premix product to the flexible container for the Lot No. 2 was measured to be less than 4.0% when the premix product was freshly prepared; less than 4.0% after the premix product was stored for 24 months at the refrigeration temperature of 2° C. to 8° C.; and less than 4.0% after the premix product was stored for 24 months at the refrigeration temperature of 2° C. to 8° C. followed by 1 month at room temperature of 23° C. to 27° C.

Here, the insulin concentration in the production tank before release (the tank release insulin concentration) was measured when the insulin premix formulation was manufactured in the production tank before filling into the flexible container. The concentration of insulin adsorption and/or absorption to the flexible container at different storage conditions and time periods was calculated by substracting the tank release insulin concentration by the insulin concentration, the concentration of the A-21 desamido impurity and the concentration of the total other insulin related substances in the flexible container at different storage conditions and time periods. Then the percentage of insulin adsorption or absorption to the flexible container was calculated by dividing the concentration of insulin adsorption and/or absorption to the flexible container by the tank release insulin concentration.

Therefore, the experimental results clearly demonstrated that the insulin premix formulation and product as disclosed and prepared herein were unexpectedly stable over 24 months of storage at refrigeration temperatures of 2° C. to 8° C. followed by 30 days of storage at room temperatures of 23° C. to 27° C., even without any added preservative, any added zinc, any added glycerol, any added surfactant or any added stabilizing excipient. The insulin adsorption and/or absorption to the flexible container was very low, less than 3.0% by weight of the total insulin even after storage for 24 months at the refrigeration temperature of 2° C. to 8° C. followed by 1 month at room temperature of 23° C. to 27° C.

Various changes and modifications to the presently preferred embodiments disclosed herein will be apparent to those skilled in the art. Such changes and modifications can be made without departing from the spirit and scope of the present subject matter and without diminishing its intended advantages. It is therefore intended that such changes and modifications be covered by the appended claims.

---

The invention claimed is:

1. A pharmaceutically acceptable insulin premix formulation comprising:
   i) about 0.1 U to about 2.0 U of insulin/mL of the total formulation, and
   ii) water,
   wherein the insulin premix formulation has a pH value of about 6.5 to 7.2,
   wherein the insulin premix formulation has no more than about 5.0% of A-21 desamido insulin impurity by weight of the total insulin based on percentage of peak area in relation to total insulin peak area as measured by reverse-phase high performance liquid chromatography (HPLC) using UV at 214 nm wavelength for detection, when freshly prepared and after storage for 24 months at a refrigeration temperature of 2° C. to 8° C. followed by 30 days at a room temperature of 23° C. to 27° C. with substantially no exposure to light during the entire storage.

2. The pharmaceutically acceptable insulin premix formulation according to claim 1, wherein the insulin premix formulation further comprises at least one tonicity adjuster.

3. The pharmaceutically acceptable insulin premix formulation according to claim 2, wherein the tonicity adjuster is sodium chloride.

4. The pharmaceutically acceptable insulin premix formulation according to claim 3, wherein the sodium chloride is about 0.80%-1.00% by weight of the formulation.

5. The pharmaceutically acceptable insulin premix formulation according to claim 1, wherein the insulin premix formulation is sterile.

6. The pharmaceutically acceptable insulin premix formulation according to claim 1, wherein the insulin premix formulation has no more than about 4.0% of A-21 desamido insulin impurity by weight of the total insulin based on percentage of peak area in relation to total insulin peak area as measured by reverse-phase high performance liquid chromatography (HPLC) using UV at 214 nm wavelength for detection, when freshly prepared and after storage for 24 months at a refrigeration temperature of 2° C. to 8° C. followed by 30 days at a room temperature of 23° C. to 27° C. with substantially no exposure to light during the entire storage.

7. The pharmaceutically acceptable insulin premix formulation according to claim 1, comprising about 0.5 U to about 2.0 U of the insulin/mL of the total formulation.

8. The pharmaceutically acceptable insulin premix formulation according to claim 1, comprising about 1.0 U of the insulin/mL of the total formulation.

9. The pharmaceutically acceptable insulin premix formulation according to claim 1, wherein the insulin premix formulation has a pH value of about 6.6 to 7.0.

10. The pharmaceutically acceptable insulin premix formulation according to claim 1, wherein the insulin premix formulation has a pH value of 6.8±1%.

11. The pharmaceutically acceptable insulin premix formulation according to claim 1, wherein the insulin premix formulation is essentially free of phenol, cresol, meta-cresol, parabens, any other added preservative, any added zinc, and any added glycerol.

12. The pharmaceutically acceptable insulin premix formulation according to claim 1, wherein the insulin premix formulation has no more than about 3.0% of A-21 desamido insulin impurity by weight of the total insulin based on percentage of peak area in relation to total insulin peak area as measured by reverse-phase high performance liquid chromatography (HPLC) using UV at 214 nm wavelength for detection, when freshly prepared and after storage for 24 months at a refrigeration temperature of 2° C. to 8° C. followed by 30 days at a room temperature of 23° C. to 27° C. with substantially no exposure to light during the entire storage.

13. The pharmaceutically acceptable insulin premix formulation according to claim 1, wherein the insulin premix formulation has no more than about 3.0% in total of insulin dimer, hexamer and other high molecular weight protein (HMWP) by weight of the total insulin, based on percentage of peak area in relation to total insulin peak area as measured by size exclusion chromatography (SEC), when freshly prepared and after storage for 24 months at a refrigeration temperature of 2° C. to 8° C. followed by 30 days at a room temperature of 23° C. to 27° C. with substantially no exposure to light during the entire storage.

14. The pharmaceutically acceptable insulin premix formulation according to claim 1, wherein the insulin in monomer form is higher than 95% by weight of the total insulin.

15. A method of manufacturing a pharmaceutically acceptable insulin premix formulation, the method comprising:
    adjusting the pH of a composition comprising water and about 0.1 U/mL to about 2.0 U/mL of insulin to a pH value of about 6.5 to 7.2,
    wherein the insulin premix formulation has no more than about 5.0% of A-21 desamido insulin impurity by weight of the total insulin based on percentage of peak area in relation to total insulin peak area as measured by reverse-phase high performance liquid chromatography (HPLC) using UV at 214 nm wavelength for detection, when freshly prepared and after storage for 24 months at a refrigeration temperature of 2° C. to 8° C. followed by 30 days at a room temperature of 23° C. to 27° C. with substantially no exposure to light during the entire storage.

16. The method according to claim 15, further comprising adding at least one buffer to the composition before, during and/or after the adjusting of the pH and mixing the composition until homogeneous.

17. The method according to claim 15, wherein the adjusting of the pH further comprises adding at least one tonicity adjuster to the composition and mixing the composition until homogeneous.

18. A pharmaceutically acceptable insulin premix product comprising a flexible container and further comprising a pharmaceutically acceptable insulin premix formulation in the flexible container, wherein the insulin premix formulation has been sterile-filled into the flexible container, and the insulin premix formulation comprises water and about 0.1 to about 10.0 U of insulin/mL of the total formulation, wherein the insulin premix formulation has a pH value of about 6.5 to 7.2.

19. The pharmaceutically acceptable insulin premix product according to claim 18, wherein the flexible container has a volume of about 1.0-1000.0 ml.

20. The pharmaceutically acceptable insulin premix product according to claim 18, wherein the flexible container has an inner surface layer contacting the insulin premix formulation, wherein the inner surface layer comprises at least one plastic material selected from the group consisting of a linear low density polyethylene (LLDPE), a polyvinyl chloride (PVC), a polypropylene (PP), a copolymer, and a modified polymer or copolymer.

21. A pharmaceutically acceptable insulin premix product comprising a flexible container and further comprising a pharmaceutically acceptable insulin premix formulation in the flexible container, wherein the insulin premix formulation has a pH value of about 6.5 to 7.2, wherein loss of insulin monomer in the insulin premix product is no more than about 8.0% by weight based on insulin monomer peak area as measured by reverse-phase high performance liquid chromatography (HPLC) using UV at 214 nm wavelength for detection, after storage for at least one month at a refrigeration temperature of 2° C. to 8° C. with substantially no exposure to light during the entire storage.

22. The pharmaceutically acceptable insulin premix product according to claim 21, wherein the insulin premix product has essentially no insulin adsorption or absorption to the flexible container throughout storage for at least one month at a refrigeration temperature of 2° C. to 8° C.

23. The pharmaceutically acceptable insulin premix product according to claim 21, wherein the pharmaceutically acceptable insulin premix formulation has less than about 5.0% of A-21 desamido insulin impurity by weight of total insulin based on percentage of peak area in relation to total insulin peak area as measured by reverse-phase high performance liquid chromatography (HPLC) using UV at 214 nm wavelength for detection, throughout storage for at least one month at a refrigeration temperature of 2° C. to 8° C. with substantially no exposure to light during the entire storage.

* * * * *